(12) United States Patent
Selover et al.

(10) Patent No.: US 8,277,491 B2
(45) Date of Patent: Oct. 2, 2012

(54) METHODS AND DEVICES FOR MINIMALLY INVASIVE SPINAL FIXATION ELEMENT PLACEMENT

(75) Inventors: Sean P. Selover, Westport, MA (US); Nancy M. Sheehy, South Boston, MA (US)

(73) Assignee: DePuy Spine, Inc., Raynham, MA (US)

( * ) Notice: Subject to any disclaimer, the term of this patent is extended or adjusted under 35 U.S.C. 154(b) by 155 days.

(21) Appl. No.: 12/726,636

(22) Filed: Mar. 18, 2010

(65) Prior Publication Data
US 2010/0174326 A1 Jul. 8, 2010

Related U.S. Application Data

(63) Continuation of application No. 10/711,704, filed on Sep. 30, 2004, now Pat. No. 7,708,763, which is a continuation-in-part of application No. 10/738,130, filed on Dec. 16, 2003, now Pat. No. 7,527,638.

(51) Int. Cl.
*A61B 17/70* (2006.01)

(52) U.S. Cl. ........ 606/279; 606/86 A

(58) Field of Classification Search ........ 600/219; 604/104, 108; 606/53, 86 A, 86 R, 99, 246, 606/279
See application file for complete search history.

(56) References Cited

U.S. PATENT DOCUMENTS

| | | | |
|---|---|---|---|
| 2,320,709 A | 6/1943 | Arnesen | |
| 2,548,729 A | 4/1951 | Kumpman | |
| 3,246,646 A | 4/1966 | Murphy | |
| 3,552,799 A | 1/1971 | Koranda | |
| 4,263,899 A | 4/1981 | Burgin | |
| 4,461,281 A | 7/1984 | Carson | |
| 4,537,448 A | 8/1985 | Ketterer | |
| 4,545,374 A | 10/1985 | Jacobson | |
| 4,573,448 A | 3/1986 | Kambin | |
| 4,686,966 A | 8/1987 | Tsai | |
| 4,765,311 A | 8/1988 | Kulik et al. | |
| 4,872,451 A | 10/1989 | Moore et al. | |

(Continued)

FOREIGN PATENT DOCUMENTS

DE 3434807 12/1985

(Continued)

OTHER PUBLICATIONS

Foley, Kevin T., "CD Horizon SEXTANT Rod Insertion System Surgical Technique" Medtronic Sofamor Danek Product Brochure (32 pages) Jul. 2002.

(Continued)

*Primary Examiner* — Eduardo C Robert
*Assistant Examiner* — Steven Cotroneo
(74) *Attorney, Agent, or Firm* — Nutter McClennen & Fish LLP

(57) ABSTRACT

Minimally invasive methods and devices for introducing a spinal fixation element into a surgical site in a patient's spinal column are provided. In one embodiment, a dissection tool is provided for separating muscles along a muscle plane without causing damage to the muscles. The dissection tool can also include a lumen extending therethrough for receiving a guide wire. The tool allows the guide wire to be positioned relative to a vertebra, and once properly positioned, the tool can be removed to allow a spinal anchor to be delivered along the guide wire and implanted into the vertebra.

11 Claims, 23 Drawing Sheets

U.S. PATENT DOCUMENTS

| | | | |
|---|---|---|---|
| 4,887,020 A | 12/1989 | Graham | |
| 4,913,134 A | 4/1990 | Luque | |
| 4,961,740 A | 10/1990 | Ray et al. | |
| 5,015,255 A | 5/1991 | Kuslich | |
| 5,024,659 A | 6/1991 | Sjostrom | |
| 5,052,372 A | 10/1991 | Shapiro | |
| 5,084,053 A | 1/1992 | Ender | |
| 5,171,279 A | 12/1992 | Mathews | |
| 5,231,973 A | 8/1993 | Dickie | |
| 5,242,443 A | 9/1993 | Kambin | |
| 5,242,446 A | 9/1993 | Steffee et al. | |
| 5,324,290 A | 6/1994 | Zdeblick et al. | |
| 5,357,983 A | 10/1994 | Mathews | |
| 5,367,983 A | 11/1994 | Pound et al. | |
| 5,395,317 A | 3/1995 | Kambin | |
| 5,439,464 A | 8/1995 | Shapiro | |
| 5,484,440 A | 1/1996 | Allard | |
| 5,520,610 A | 5/1996 | Giglio et al. | |
| 5,569,248 A | 10/1996 | Mathews | |
| 5,647,873 A | 7/1997 | Errico et al. | |
| 5,728,097 A | 3/1998 | Mathews | |
| 5,741,261 A * | 4/1998 | Moskovitz et al. | 606/79 |
| 5,749,884 A | 5/1998 | Benderev et al. | |
| 5,762,629 A | 6/1998 | Kambin | |
| 5,766,221 A | 6/1998 | Benderev et al. | |
| 5,817,094 A | 10/1998 | Errico et al. | |
| 5,891,147 A | 4/1999 | Moskovitz et al. | |
| 5,897,590 A | 4/1999 | Donovan | |
| 5,910,141 A | 6/1999 | Morrison et al. | |
| 5,928,139 A | 7/1999 | Koros et al. | |
| 5,931,777 A | 8/1999 | Sava | |
| 5,954,635 A | 9/1999 | Foley et al. | |
| 5,984,923 A | 11/1999 | Breard | |
| 6,033,406 A | 3/2000 | Mathews | |
| 6,139,493 A | 10/2000 | Koros et al. | |
| 6,159,179 A | 12/2000 | Simonson | |
| 6,183,472 B1 | 2/2001 | Lutz | |
| 6,200,322 B1 | 3/2001 | Branch et al. | |
| 6,224,545 B1 | 5/2001 | Cocchia et al. | |
| 6,226,548 B1 | 5/2001 | Foley et al. | |
| 6,235,028 B1 | 5/2001 | Brumfield et al. | |
| 6,299,616 B1 | 10/2001 | Beger | |
| 6,331,179 B1 | 12/2001 | Freid et al. | |
| 6,371,968 B1 | 4/2002 | Kogasaka et al. | |
| 6,440,133 B1 | 8/2002 | Beale et al. | |
| 6,485,491 B1 | 11/2002 | Farris et al. | |
| 6,520,907 B1 | 2/2003 | Foley et al. | |
| 6,530,926 B1 | 3/2003 | Davison | |
| 6,530,929 B1 | 3/2003 | Justis et al. | |
| 6,540,749 B2 | 4/2003 | Schafer et al. | |
| 6,554,831 B1 | 4/2003 | Rivard et al. | |
| 6,607,530 B1 | 8/2003 | Carl et al. | |
| 6,648,888 B1 | 11/2003 | Shluzas | |
| 6,652,527 B2 | 11/2003 | Zucherman et al. | |
| 6,660,006 B2 | 12/2003 | Markworth et al. | |
| 6,666,891 B2 | 12/2003 | Boehm, Jr. et al. | |
| 6,740,086 B2 | 5/2004 | Richelsoph | |
| 6,740,089 B2 | 5/2004 | Haider | |
| 6,743,231 B1 | 6/2004 | Gray et al. | |
| 6,749,614 B2 | 6/2004 | Teitelbaum et al. | |
| 6,793,656 B1 | 9/2004 | Mathews | |
| 6,821,277 B2 | 11/2004 | Teitelbaum | |
| 6,849,064 B2 | 2/2005 | Hamada | |
| 6,899,713 B2 | 5/2005 | Shaolian et al. | |
| 6,929,647 B2 | 8/2005 | Cohen | |
| 6,964,667 B2 | 11/2005 | Shaolian et al. | |
| 7,083,621 B2 | 8/2006 | Shaolian et al. | |
| 7,179,061 B2 | 2/2007 | Horton et al. | |
| 7,179,225 B2 | 2/2007 | Shluzas et al. | |
| 7,250,052 B2 | 7/2007 | Landry et al. | |
| 7,306,603 B2 | 12/2007 | Boehm, Jr. et al. | |
| 7,527,638 B2 | 5/2009 | Anderson et al. | |
| 2001/0001119 A1 | 5/2001 | Lombardo | |
| 2002/0011600 A1 | 1/2002 | Kurahashi et al. | |
| 2002/0022764 A1 * | 2/2002 | Smith et al. | 600/114 |
| 2002/0049368 A1 | 4/2002 | Ritland | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0116000 A1 | 8/2002 | Zucherman et al. | |
| 2002/0116006 A1 | 8/2002 | Cohen | |
| 2002/0123668 A1 | 9/2002 | Ritland | |
| 2002/0138077 A1 | 9/2002 | Ferree | |
| 2002/0161368 A1 | 10/2002 | Foley et al. | |
| 2002/0169448 A1 | 11/2002 | Vanacker | |
| 2002/0198526 A1 | 12/2002 | Shaolian et al. | |
| 2003/0060826 A1 | 3/2003 | Foley et al. | |
| 2003/0083657 A1 | 5/2003 | Drewry et al. | |
| 2003/0083688 A1 * | 5/2003 | Simonson | 606/191 |
| 2003/0083689 A1 | 5/2003 | Simonson | |
| 2003/0130659 A1 | 7/2003 | Haider | |
| 2003/0191371 A1 | 10/2003 | Smith et al. | |
| 2003/0195549 A1 | 10/2003 | Davison et al. | |
| 2003/0195550 A1 | 10/2003 | Davison et al. | |
| 2003/0195551 A1 | 10/2003 | Davison et al. | |
| 2003/0199885 A1 | 10/2003 | Davison et al. | |
| 2003/0208203 A1 | 11/2003 | Lim et al. | |
| 2003/0216768 A1 | 11/2003 | Gitis et al. | |
| 2003/0229347 A1 | 12/2003 | Sherman et al. | |
| 2004/0006301 A1 | 1/2004 | Sell et al. | |
| 2004/0006344 A1 * | 1/2004 | Nguyen et al. | 606/72 |
| 2004/0039384 A1 | 2/2004 | Boehm et al. | |
| 2004/0082961 A1 | 4/2004 | Teitelbaum | |
| 2004/0138662 A1 | 7/2004 | Landry et al. | |
| 2004/0143265 A1 | 7/2004 | Landry et al. | |
| 2004/0162560 A1 | 8/2004 | Raynor et al. | |
| 2004/0172022 A1 * | 9/2004 | Landry et al. | 606/61 |
| 2004/0260284 A1 | 12/2004 | Parker | |
| 2004/0267277 A1 | 12/2004 | Zannis et al. | |
| 2005/0038432 A1 * | 2/2005 | Shaolian et al. | 606/61 |
| 2005/0038434 A1 | 2/2005 | Mathews | |
| 2005/0065517 A1 | 3/2005 | Chin | |
| 2005/0080418 A1 | 4/2005 | Simonson et al. | |
| 2005/0085813 A1 * | 4/2005 | Spitler et al. | 606/61 |
| 2005/0096748 A1 | 5/2005 | Yoon | |
| 2005/0131407 A1 | 6/2005 | Sicvol et al. | |
| 2005/0154389 A1 | 7/2005 | Selover et al. | |
| 2005/0171540 A1 | 8/2005 | Lim et al. | |
| 2005/0182410 A1 | 8/2005 | Jackson | |
| 2005/0192570 A1 | 9/2005 | Jackson | |
| 2005/0192579 A1 | 9/2005 | Jackson | |

FOREIGN PATENT DOCUMENTS

| | | |
|---|---|---|
| DE | 10027988 A1 | 1/2002 |
| DE | 29810798 | 5/2004 |
| EP | 0528562 | 2/1993 |
| EP | 1190678 | 3/2002 |
| FR | 2729291 A1 | 7/1996 |
| FR | 2796545 | 1/2001 |
| WO | 9205742 A1 | 4/1992 |
| WO | 9308745 A1 | 5/1993 |
| WO | 2004017847 | 3/2004 |
| WO | 2004041100 | 5/2004 |
| WO | 2005041799 | 5/2005 |

OTHER PUBLICATIONS

DePuy AcroMed Product Brochure "micro'TLIF, A Mini-Open and Intermuscular Transforaminal Lumbar Interbody Fusion" Aperture Spinal System, (22 pages) Oct. 2002.

Speer, et al., "An Arthroscopic Technique for Anterior Stabiliatin of the Shoulder with A Bioabsorbable Tack," J. Bone Joint Surg Am. 1996; 78:1801-7.

Muller, et al., "A Keyhole Approach for Endoscopically Assisted Pedicle Screw Fixation in Lumbar Spine Instability," Neurosurgery, vol. 47, No. 1, Jul. 2000.

The Dilation Retractor System, Bright Medical Instruments, Boca Raton, FL, (Apr. 2001).

Search Report from related EP 04 81 2446 dated Dec. 2, 2008.

Wiltse LL and Spencer, CW, "New Uses and Refinements of the Paraspinal Approach," Jun. 6, 1988, Lippincott Williams and Wilkins, SPINE Jun. 1988;13(6):696-706.

Jampel, Robert and Charles Bloomgarden. "Individual extraocular muscle function from faradic stimulation of the oculomotor and trochlear nerves of the macaque," Investigative Opthamology, Jun. 1963, 265-266.

* cited by examiner

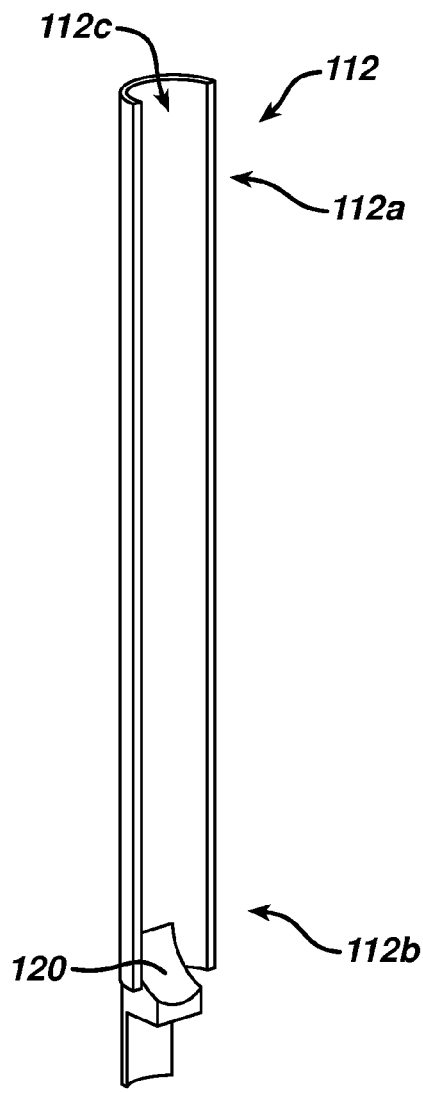
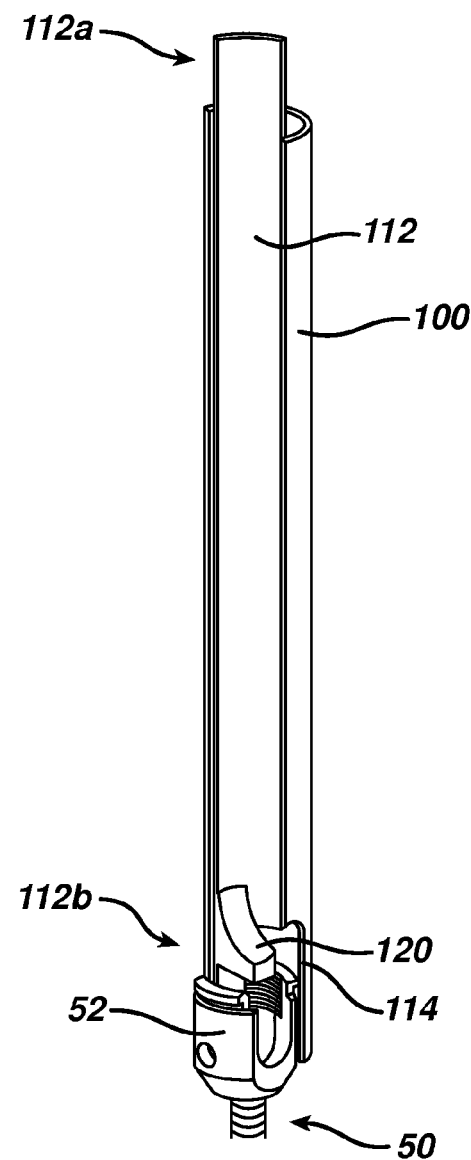
FIG. 3A
FIG. 3B

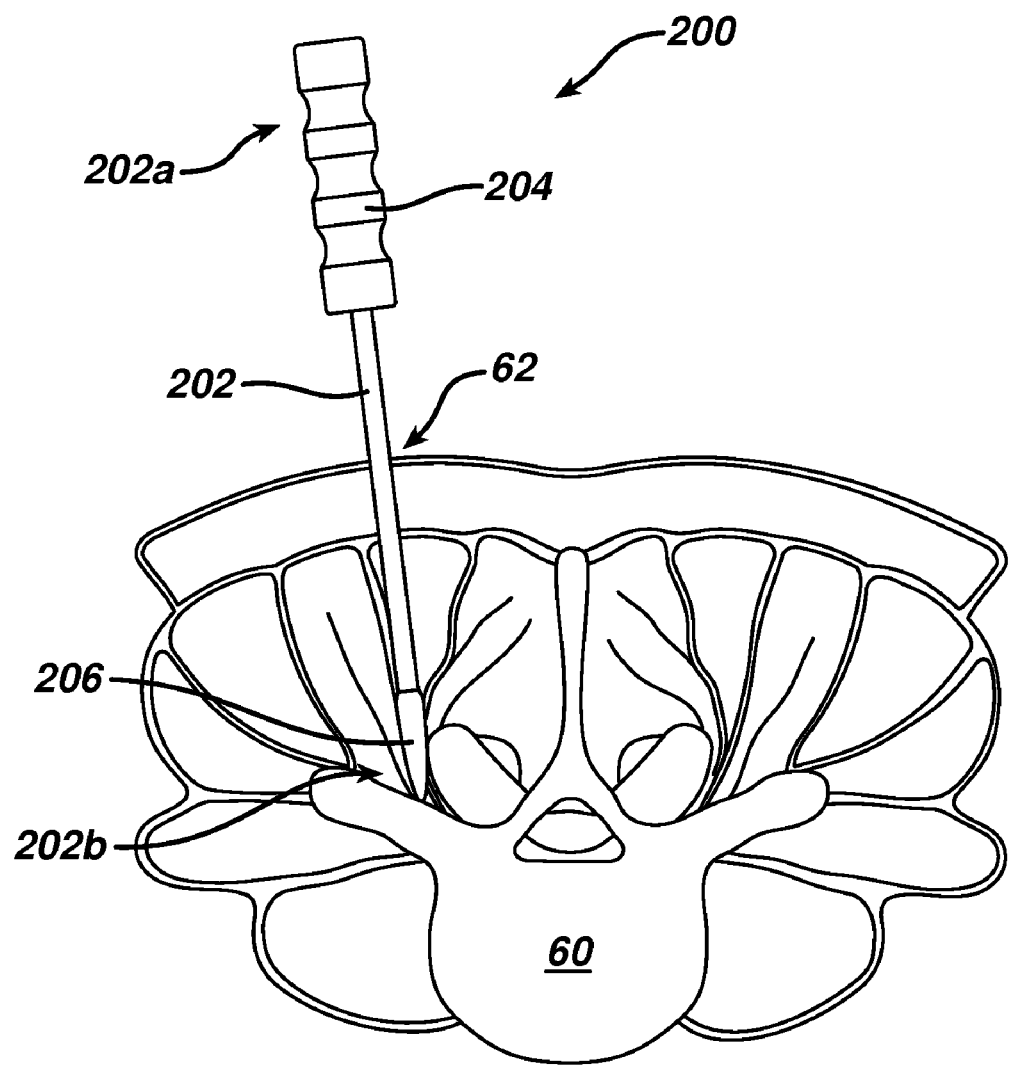

FIG. 5F
FIG. 5G
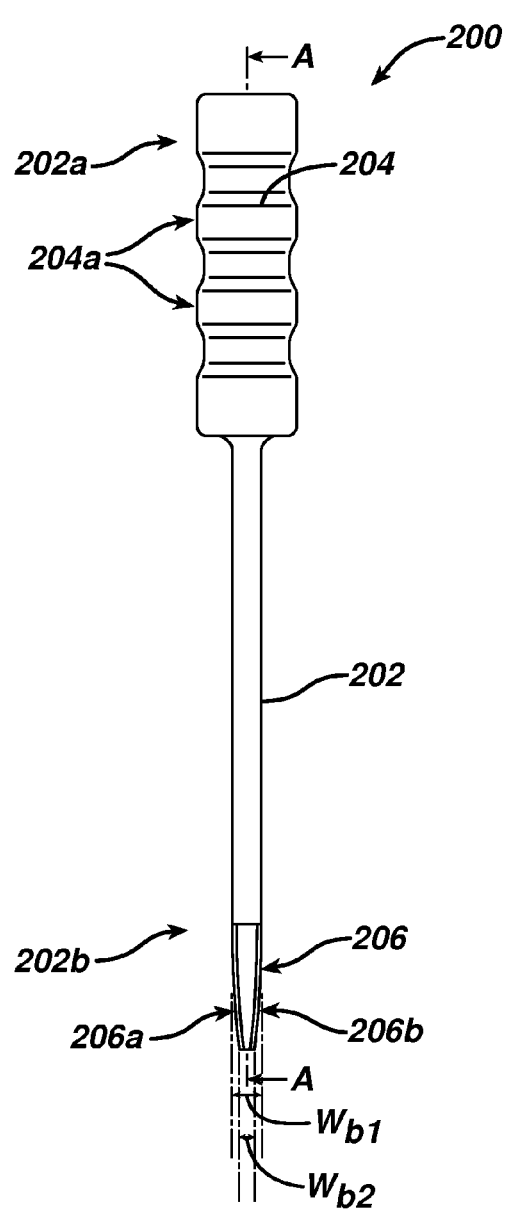
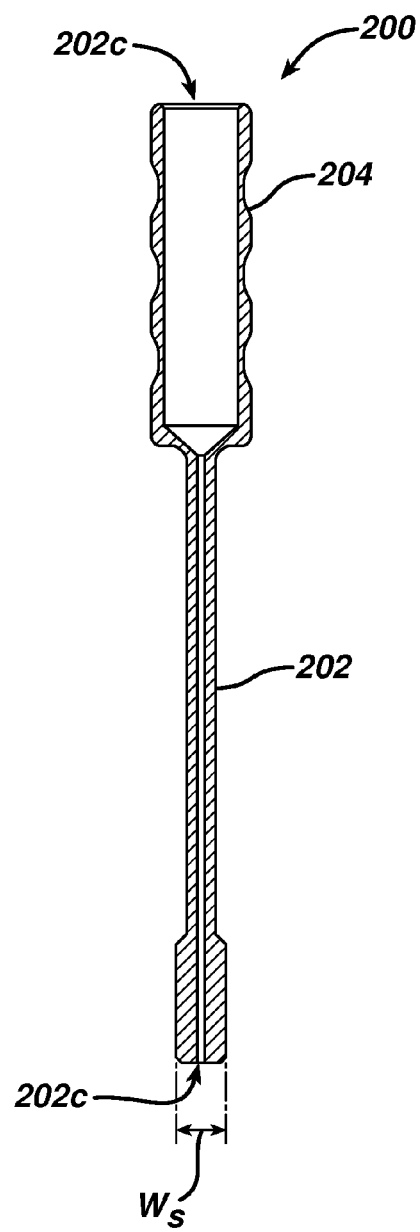

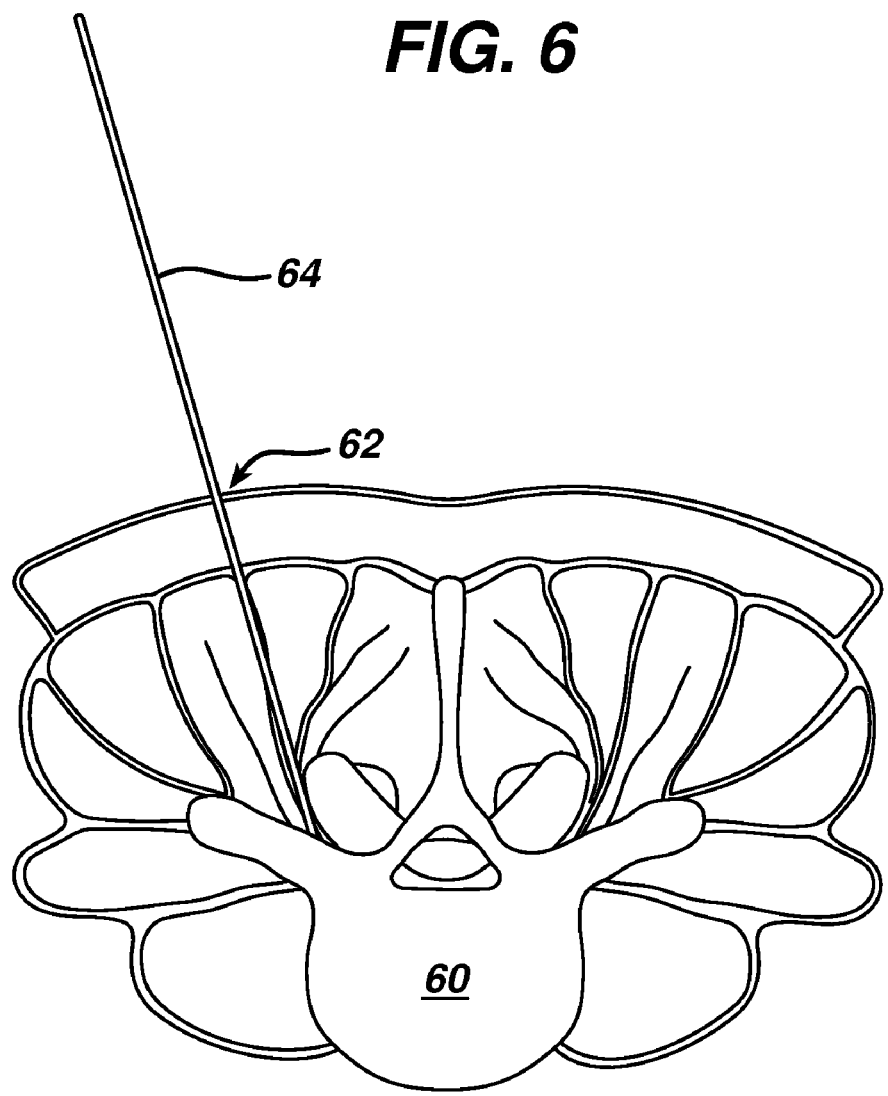

METHODS AND DEVICES FOR MINIMALLY INVASIVE SPINAL FIXATION ELEMENT PLACEMENT

CROSS-REFERENCE TO RELATED APPLICATIONS

The present application is a continuation of U.S. patent application Ser. No. 10/711,704 filed on Sep. 30, 2004 and entitled "Methods and Devices for Spinal Fixation Element Placement," now U.S. Pat. No. 7,708,763, which is a continuation-in-part of U.S. patent application Ser. No. 10/738,130 filed on Dec. 16, 2003 and entitled "Methods and Devices for Spinal Fixation Element Placement," now U.S. Pat. No. 7,527,638. These references are hereby incorporated by reference in their entireties.

FIELD OF THE INVENTION

This application relates to tools for use in spinal surgery, and in particular to minimally invasive methods and devices for introducing a spinal fixation element to one or more spinal anchor sites within a patient's spine.

BACKGROUND OF THE INVENTION

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure, and increase patient trauma and recovery time.

Accordingly, there remains a need for improved minimally invasive devices and methods for introducing a spinal fixation element into a patient's spine.

SUMMARY OF THE INVENTION

Disclosed herein are minimally invasive methods and devices for delivering a spinal fixation element to one or more spinal anchor sites in a patient's spinal column. In one embodiment, a minimally invasive surgical method is provided that includes forming an incision through tissue located adjacent to a vertebra in a patient's spinal column, and inserting a blunt tip of a tool through the incision while manipulating the tool along the muscle plane extending between the incision and the vertebra to separate the muscles. The blunt tip preferably has a substantially planar configuration, or it includes at least one surface that is substantially planar. In an exemplary embodiment, the blunt tip of the tool is adapted to separate the longissimus thoracis and multifidus muscles. The method can also include inserting a guide wire through a lumen extending through the tool. The guide wire is preferably positioned such that it extends into the vertebra. Once properly positioned, the tool can be removed leaving the guide wire in position to receive a spinal implant, such as a spinal anchor, which is preferably delivered to the vertebra along the guide wire. The aforementioned method can be repeated to deliver one or more additional implants to adjacent vertebrae. A spinal fixation element, such as a spinal rod, can then be delivered along one of the pathways extending to a vertebral body, and it can be coupled to the implant implanted within the adjacent vertebrae. In an exemplary embodiment, the fixation element may be inserted through one of the pathways in an orientation substantially parallel to a longitudinal axis of the first pathway. In certain exemplary embodiments, the spinal fixation element may be delivered through a cannula that extends along the pathway from the tissue surface to one of the vertebra.

In another exemplary embodiment, a medical device kit for use in spinal surgery may include a tissue dissection tool have a blunt member formed on a distal end thereof and adapted to separate muscles along a muscle plane without causing damage to the muscles. The exemplary tissue dissection tool may include a lumen extending therethrough. The kit may also include at least one guide wire that is adapted to be disposed through the lumen in the tissue dissection tool, and at least one spinal anchor that is adapted to be implanted in a vertebral body. The kit can may also include at least one cannula that is adapted to provide a pathway from a tissue surface to a vertebral body for delivering a spinal anchor to the vertebral body, and/or at least one spinal fixation element that is adapted to couple to and extend between at least two spinal anchors.

In yet another embodiment of the present invention, a spinal anchor is percutaneously delivered to a vertebral body having a percutaneous access device mated thereto and having a lumen extending therethrough and defining a longitudinal axis. A spinal fixation element is then advanced through the lumen in the percutaneous access device in a first, lengthwise orientation in which the fixation element is substantially parallel to the longitudinal axis of the percutaneous access device. The spinal fixation element can then be manipulated to extend in a second orientation, such that the fixation element is angled with respect to the first orientation, to position the spinal fixation element in relation to the spinal anchor. The method can also include the step of percutaneously delivering a second spinal anchor to a vertebral body with a second percutaneous access device mated thereto. The spinal fixation element thus preferably extends between the first and second spinal anchors in the second orientation.

In an exemplary embodiment, the percutaneous access device is in the form of an elongate, generally cylindrical tube that is adapted for percutaneous delivery and that is adapted to mate to a spinal anchor. The tube can include proximal and distal ends with a lumen extending therebetween. The lumen is adapted to transport a spinal fixation element therethrough in a first, lengthwise orientation that is substantially parallel to a longitudinal axis of the percutaneous access device, and to deliver the spinal fixation element to a spinal anchor site in a second orientation that is angled with respect to the first orientation, and more preferably that is substantially parallel to a patient's spinal column. The percutaneous access device can also include at least one sidewall opening extending from the distal end of the elongate, generally cylindrical tube through at least a portion thereof for facilitating transition of a spinal fixation element from the first orientation to the second orientation. In one embodiment, the device includes opposed sidewall openings formed therein adjacent to the distal end thereof. The device can also optionally or alternatively include a guide member formed within the lumen that is adapted to direct a spinal fixation element disposed therein from the first orientation to the second orientation. The guide member can be, for example, a sloped shelf formed within the lumen of the percutaneous access device.

In another embodiment of the present invention, a minimally invasive method for delivering a spinal fixation element to a spinal anchor site in a patient's spinal column is provided. The method includes the step of introducing a spinal fixation element into a lumen of a percutaneous access device. The lumen preferably forms a pathway to a spinal anchor disposed in a patient's vertebra. In an exemplary embodiment, the percutaneous access device has an outer diameter that is substantially the same as or less than a largest width of the spinal anchor to which it is attached. A person skilled in the art will appreciate that the outer diameter of the percutaneous access device can optionally be greater than the outer diameter of the spinal anchor to which it is attached. The method further includes the steps of advancing the spinal fixation element distally through the lumen in a first, lengthwise orientation that is substantially parallel to a longitudinal axis of the percutaneous access device, and manipulating the spinal fixation element into a second orientation that is substantially parallel to the patient's spinal column. The spinal fixation element can then be positioned relative to one or more spinal anchors.

In other aspects of the present invention, a minimally invasive surgical method is provided that includes the steps of making a first percutaneous incision in a patient, and creating a first pathway from the first percutaneous incision to an anchor site on a first vertebral body. Preferably, the pathway is a minimally invasive pathway such that it leads only to a single anchor site, rather than multiple anchor sites. This can be achieved, for example, by a percutaneous access device that has a substantially uniform width from the first percutaneous incision to a first anchor site on a first vertebral body. In an exemplary embodiment, the first pathway has a width that is substantially equal to or less than a width of the first percutaneous incision, and/or that is substantially equal to or less than a width of a first anchor. The method also includes the steps of placing a first anchor through the first percutaneous incision, advancing the first anchor along the first pathway to the single anchor site, and placing a fixation element through the first pathway in an orientation substantially parallel to a longitudinal axis of the first pathway.

In a further embodiment, a second percutaneous incision can be made in a patient, and a second minimally invasive pathway can be created from the second percutaneous incision to a second anchor site on a second vertebral body. A second anchor is then advanced along the second pathway to the second anchor site on the second vertebral body.

Additional methods and devices for introducing a spinal fixation element to one or more spinal anchor sites are also provided.

BRIEF DESCRIPTION OF THE DRAWINGS

FIG. 3A is a partially cut-away view of another embodiment of a percutaneous access device having a guide member formed therein;

FIG. 3B is a partially cut-away view of the percutaneous access device shown in FIG. 3A having a sleeve disposed there around and a spinal anchor mated thereto;

FIG. 5D is an end view of the vertebra shown in FIG. 5C showing the tool further inserted along the dissected muscle plane;

FIG. 5F is a side view of the tool shown in FIGS. 5C-5E;

FIG. 5G is a cross-sectional view of the tool shown in FIG. 5F taken along line A-A;

FIG. 6 is an end view of the vertebra shown in FIG. 4 showing placement of a guide wire through the incision and into the patient's vertebra;

DETAILED DESCRIPTION OF THE INVENTION

The present invention provides minimally invasive methods and devices for introducing a spinal fixation element into a surgical site in a patient's spinal column. In general, the method involves advancing a spinal fixation element in a lengthwise orientation along a minimally invasive pathway that extends from a minimally invasive percutaneous incision to a spinal anchor site. In an exemplary embodiment, a percutaneous access device is used to create the minimally invasive pathway for receiving the spinal fixation element and for delivering the fixation element to a spinal anchor site. The spinal fixation element is preferably inserted through a lumen in the percutaneous access device in a lengthwise orientation, such that the spinal fixation element is oriented substantially parallel to a longitudinal axis of the percutaneous access device. As the spinal fixation element approaches or reaches the distal end of the pathway, the spinal fixation element can be manipulated to orient it at a desired angle with respect to the percutaneous access device, preferably such that the spinal fixation element is substantially parallel to the patient's spinal column. The spinal fixation element can then optionally be positioned to couple it, either directly or indirectly, to one or more spinal anchors. A fastening element or other closure mechanism, if necessary, can then be introduced into the spinal anchor site to fixedly mate the spinal fixation element to the anchor(s).

The methods and devices of the present invention are particularly advantageous in that they can be achieved using one or more minimally invasive percutaneous incisions for accessing the spinal column. Such incisions minimize damage to intervening tissues, and they reduce recovery time and post-operative pain. The present invention also advantageously provides techniques for delivering spinal fixation elements and anchors along a minimally invasive pathway, thus eliminating the need to create a large working area at the surgical site.

Figure 1:
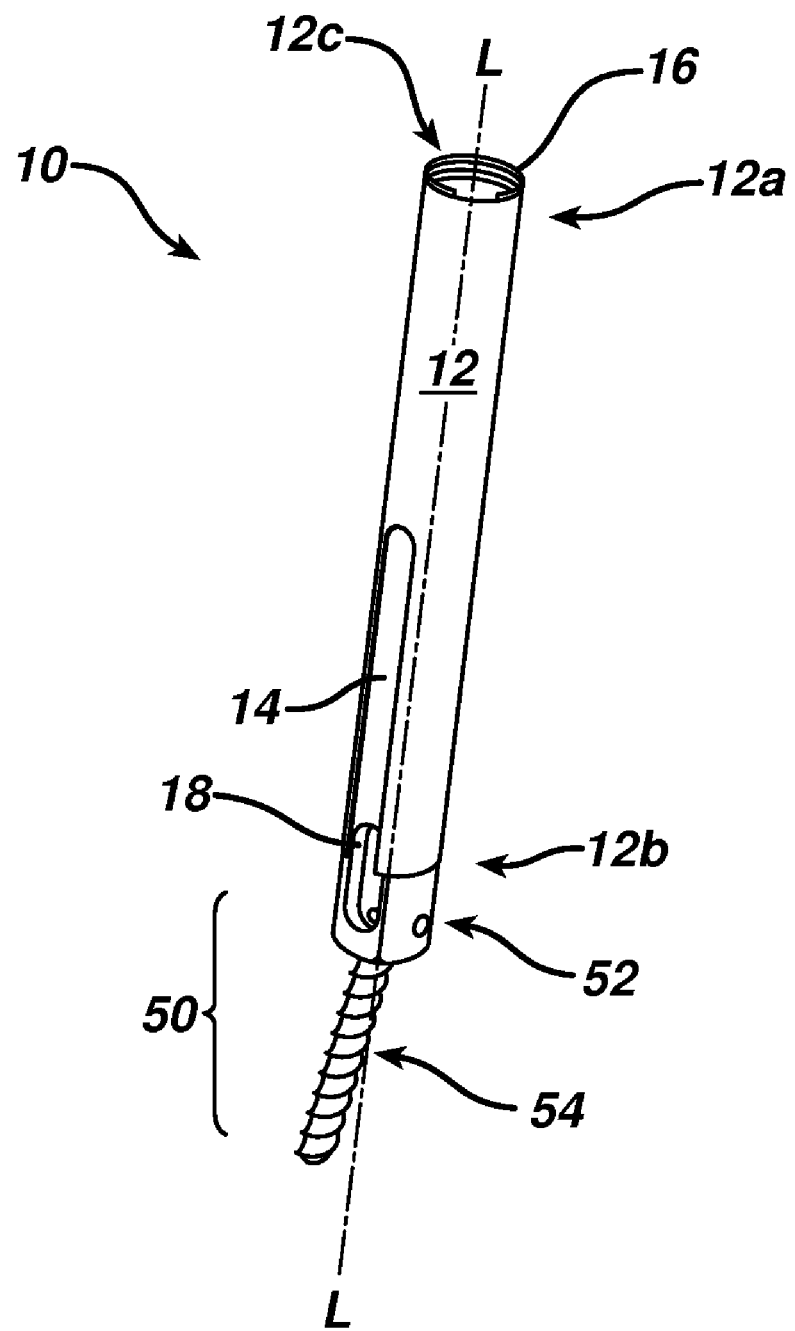
FIG. 1 is a perspective view of a percutaneous access device coupled to an anchor according to one embodiment of the present invention.
Figure 2:
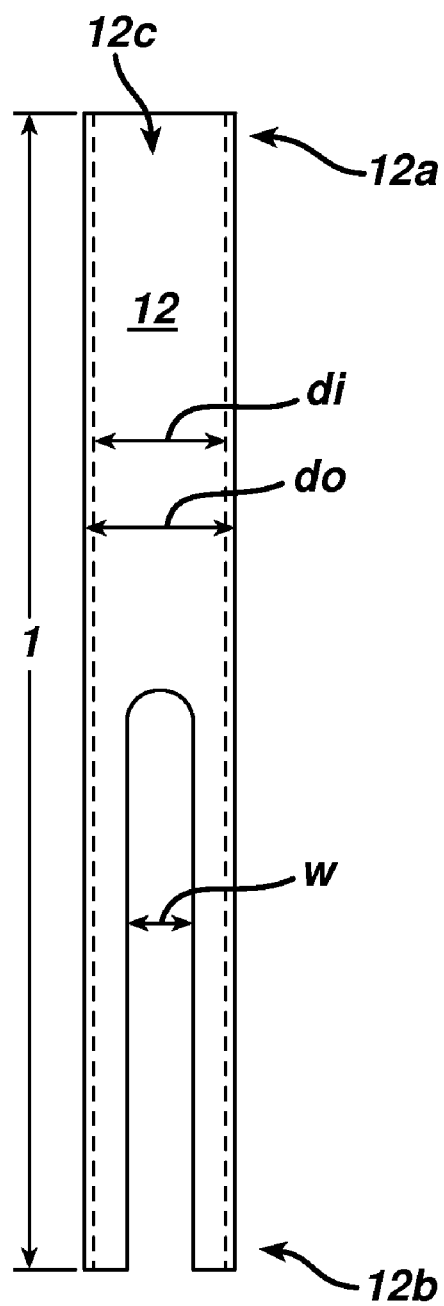
FIG. 2 is a cross-sectional view taken along the longitudinal axis of the percutaneous access device shown in FIG. 1.

While a variety of devices can be used to perform the methods of the present invention, FIGS. 1 and 2 illustrate an exemplary embodiment of a percutaneous access device 12 that is mated to a spinal anchor 50 (FIG. 1) to form a spinal implant assembly 10. As shown, the device 12 is in the form of a generally elongate, cylindrical tube having an inner lumen 12c formed therein and defining a longitudinal axis L that extends between proximal and distal ends 12a, 12b. The size of the access device 12 can vary depending on the intended use, but it should have a length l that allows the proximal end 12a of the access device 12 to be positioned outside the patient's body, while the distal end 12b of the access device 12 is coupled to, or positioned adjacent to, a spinal anchor, e.g., anchor 50, that is disposed in a vertebra in a patient's spine. The access device 12 is also preferably adapted to provide a minimally invasive pathway for the delivery of a spinal fixation element, and in particular, the percutaneous access device 12 should also be adapted to be implanted through a minimally invasive percutaneous incision, which is a relatively small incision that typically has a length that is less than a diameter or width of the device being inserted therethrough.

In an exemplary embodiment, the device 12 has an inner diameter $d_i$ that is sufficient to allow a spinal fixation element to be introduced therethrough, preferably in a lengthwise orientation. The inner diameter $d_i$ can also optionally be configured to allow a driver mechanism to be introduced therethrough for applying a closure mechanism to lock the spinal fixation element in relation to a spinal anchor. The outer diameter $d_o$ of the access device 12 can also vary, and it can be the same as, less than, or greater than an outer diameter $d_r$ of the spinal anchor. In the illustrated embodiment, the access device 12 has an outer diameter $d_o$ that is substantially the same as an outer diameter $d_r$ of the spinal anchor, which, as illustrated in FIG. 1, is the receiver head 52 of a spinal screw 50. This is particularly advantageous in that the size of the incision does not need to be any larger than necessary. The matching outer diameters $d_o$, $d_r$ of the access device 12 and the anchor 50 also allow the access device 12 and/or the anchor 50 to be introduced through a cannula. If the access device 12 is mated to the anchor 50, the matching outer diameters $d_o$, $d_r$ also allows a sleeve or other device to be slidably disposed there around to prevent disengagement between the access device 12 and the anchor 50. In another, exemplary embodiment, the outer diameter $d_o$ of the access device 12 can be slightly greater than the outer diameter $d_r$ of the spinal anchor. By way of non-limiting example, where a receiver head of the spinal anchor has an outer diameter $d_r$ that is about 13 mm, the access device 12 preferably has an outer diameter $d_o$ that is about 15 mm.

The percutaneous access device 12 also preferably includes at least one sidewall opening or slot 14 formed therein, and more preferably it includes two opposed sidewall openings (only one opening 14 is shown) formed therein and extending proximally from the distal end 12b thereof. The openings 14 allow a spinal fixation element to be introduced through the device 12 in a first, lengthwise orientation, in which the spinal fixation element is substantially parallel to the longitudinal axis L of the access device 12. The spinal fixation element can then to be manipulated to extend at an angle with respect to the first orientation, such that the fixation element extends in a direction substantially transverse to the longitudinal axis L of the access device 12, for example, in a direction that is substantially parallel to the patient's spine. Since the length L of the spinal fixation element will necessarily be greater than the inner diameter $d_i$ of the access device 12, the openings 14 allow the spinal fixation element to pass therethrough while being transitioned from the first, lengthwise orientation to the second orientation. A person skilled in the art will appreciate that the exact position of the spinal fixation element with respect to the longitudinal axis L will of course vary depending on the configuration of the spinal fixation element.

The shape and size of each opening 14 can vary, but the opening(s) 14 should be effective to allow movement of the spinal fixation element from the first orientation to the second orientation. In an exemplary embodiment, the openings 14 extend over about half of the length, or less than half of the length, of the percutaneous access device 12. The shape of each slot 14 can be generally elongate, and they should each have a width w that is sufficient to accommodate the diameter of the spinal fixation element. A person skilled in the art will appreciate that the percutaneous access device 12 can include any number of sidewall openings having any shape that is sufficient to allow a spinal fixation element to be moved from the first orientation to the second orientation.

In another embodiment of the present invention, shown in FIGS. 3A-3B, the percutaneous access device 112 can also optionally include a guide member 120 formed within the distal end 112b of the lumen 112c to help guide the spinal fixation element from the first orientation to the second orientation. The guide member 120 can have a variety of configurations, but it should be effective to guide the spinal fixation element from the first orientation toward the anchor 50 attached to, or positioned adjacent to, the access device 112, and optionally toward anchor(s) implanted in adjacent vertebrae. In an exemplary embodiment, as shown, the guide member 120 is in the form of a sloped shelf formed within the inner lumen 112c of the access device 112 and preferably positioned opposite to a single sidewall slot 114 formed in the access device 112. The sloped shelf 120 can vary in shape and size depending on the type of fixation element being used and/or the geometry of the access device. In use, as the leading end of a spinal fixation element, such as a spinal rod, contacts the shelf 120, the shelf 120 begins to direct the spinal fixation element into the second orientation, thereby causing the spinal fixation element to extend in a direction that is substantially transverse to the axis L of the device 112, and that is preferably substantially parallel to the patient's spinal column. The spinal fixation element can then be manipulated to position it in relation to one or more spinal anchors, as will be discussed in more detail below.

Referring back to FIG. 1, in use, the percutaneous access device 12 can be adapted to attach to a spinal anchor 50. Accordingly, the distal end 12c of the percutaneous access device 12 can include one or more mating elements 18 formed thereon or therein for engaging the anchor 50. Suitable mating elements include, for example, threads, a twist-lock engagement, a snap-on engagement, or any other technique known in the art, and in an exemplary embodiment the mating elements are formed on opposed inner surfaces of the distal end 12b of the access device 12. A sleeve 100 (partially shown in FIG. 3B) or other device, preferably having sidewall openings (not shown) that correspond with the sidewall openings 14 formed in the percutaneous access device 12, can also be placed over the percutaneous access device 12, and optionally over the implant 50 as well, to prevent disengagement of the access device 12 from the implant 50 during use. Exemplary techniques for mating the percutaneous access device 12 to an anchor are disclosed in U.S. Pat. No. 7,179,261 entitled "Percutaneous Access Devices and Bone Anchor Assemblies," filed on Dec. 16, 2003. A person skilled in the art will appreciate that a variety of other techniques can be used to removably mate the percutaneous access device to an anchor.

For reference purposes, FIG. 1 illustrates an exemplary spinal anchor for use with the methods and devices of the present invention. A person skilled in the art will appreciate that a variety of anchors can be used with the devices and methods of the present invention, including, for example, spinal screws, hooks, bolts, and wires. FIG. 1 illustrates a spinal screw that includes a distal, bone-engaging portion, e.g., a threaded shank 54, and a proximal, U-shaped, receiver head 52 that is adapted to seat a spinal fixation element, preferably a spinal rod (not shown). The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

FIGS. 4A-17 show a minimally invasive method of implanting a spinal fixation element. While the method is shown and described in connection with the percutaneous access device 12 and spinal screw 50 disclosed herein, a person skilled in the art will appreciate that the method is not limited to use with such devices, and that a variety of other devices known in the art can be used. Moreover, while only two access devices 12, 12' and two anchors 50, 50' are shown in FIGS. 4-14, the method of the present invention can be performed using any number of access devices and anchors. The method can also be performed using only some of the method steps disclosed herein, and/or using other methods known in the art.

Figure 4A:
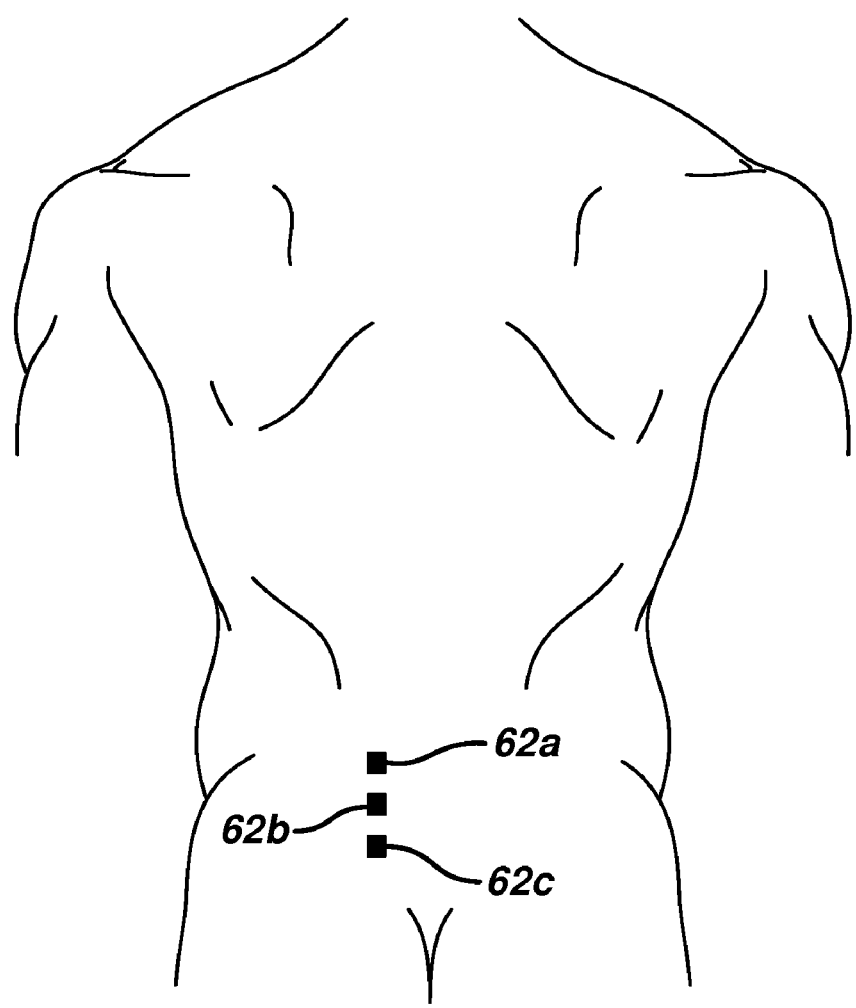
FIG. 4A is a posterior view of three percutaneous incisions formed in the thoracolumbar fascia of a patient's back.
Figure 4B:
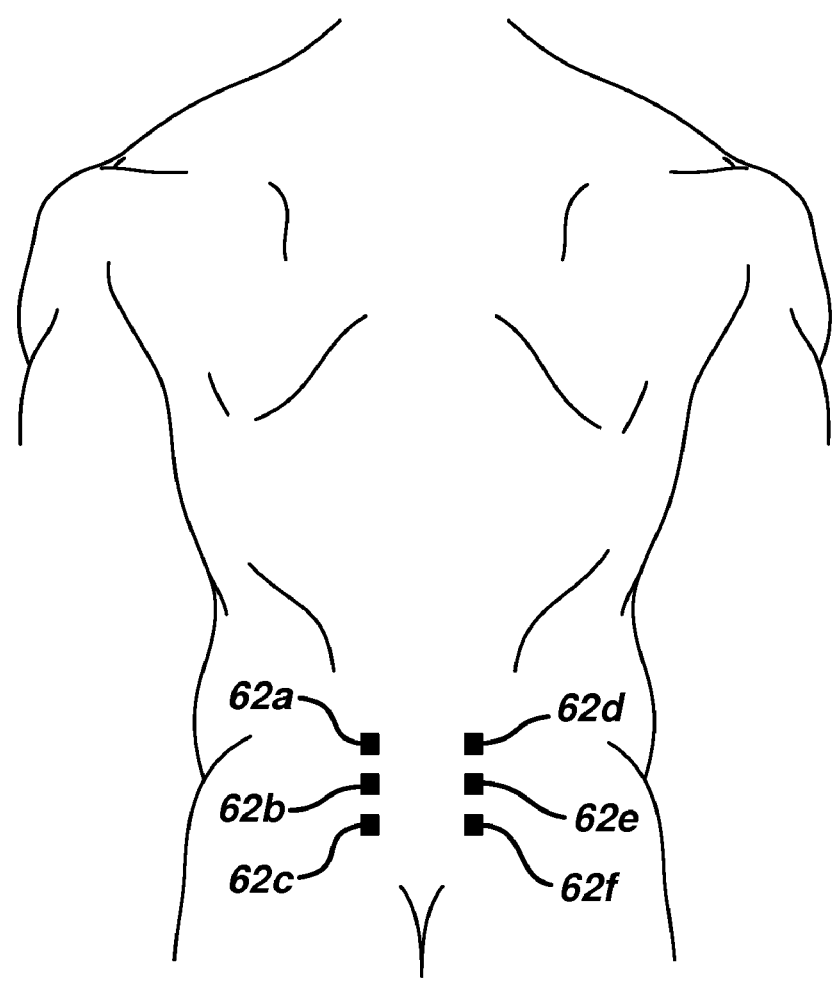
FIG. 4B is a posterior view of six percutaneous incisions formed in the thoracolumbar fascia of a patient's back.

The procedure preferably begins by forming a minimally invasive percutaneous incision through the tissue located adjacent to the desired implant site. While the location, shape, and size of the incision will depend on the type and quantity of spinal anchors being implanted, FIG. 4A illustrates three midline minimally invasive percutaneous incisions 62a-c formed on one side of three adjacent vertebra in the thoracolumbar fascia in the patient's back, and FIG. 4B illustrates three additional midline minimally invasive percutaneous incisions 62d-f formed on the opposite side of the three adjacent vertebra in the thoracolumbar fascia in the patient's back. Each incision 62a-f is a stab incision that has a diameter of about 10-20 mm in diameter, however this can vary depending on the procedure. In an exemplary embodiment, each incision 62a-f has a diameter that is equal to or less than a largest diameter of the anchor and/or the percutaneous access device being inserted therethrough.

Figure 5A:
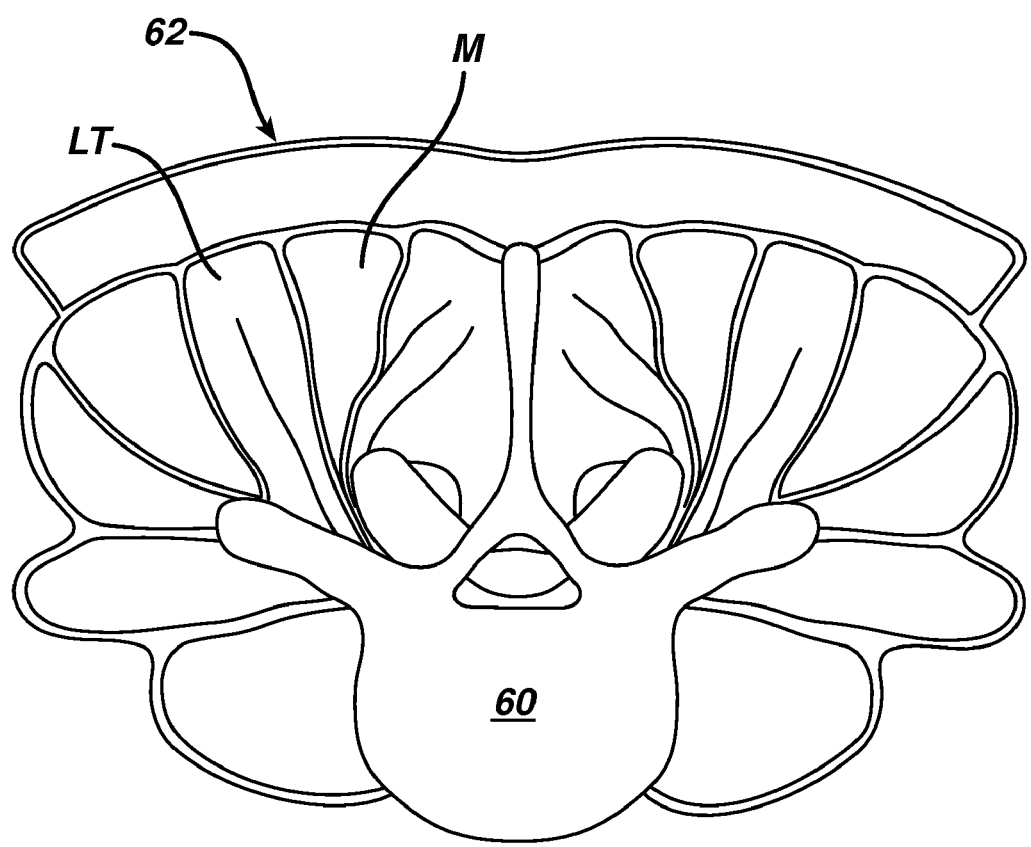
FIG. 5A is an end view showing a blunt dissection of the muscles surrounding a patient's vertebra.
Figure 5B:
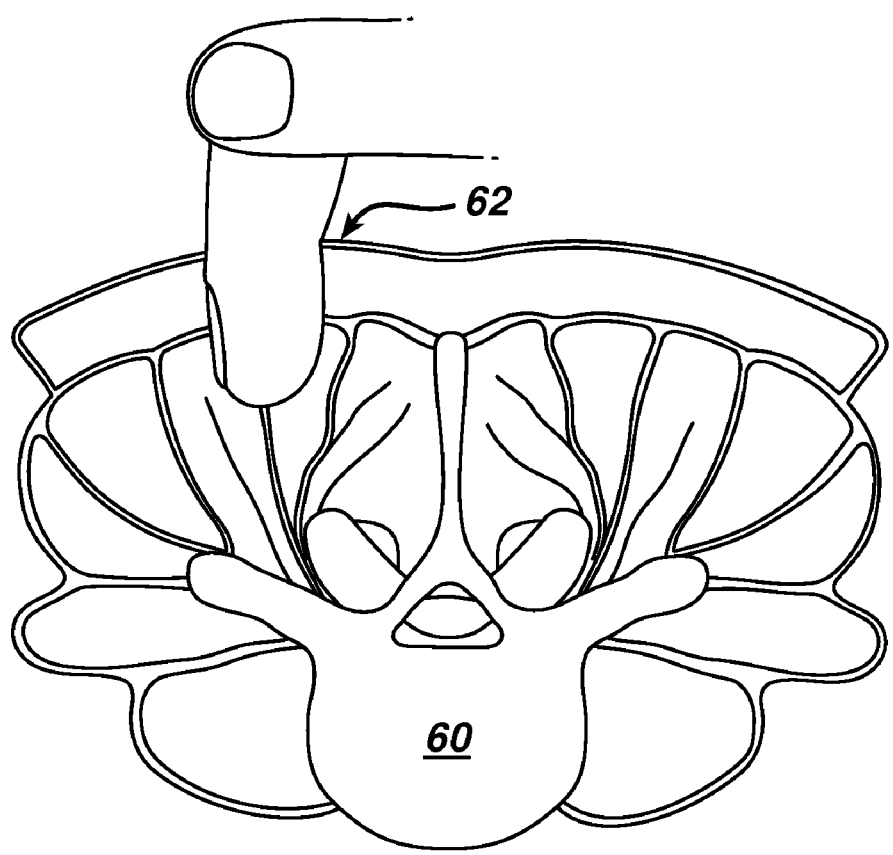
FIG. 5B is an end view of the vertebra shown in FIG. 5A showing a technique using a finger for separating the muscles along the dissected muscle plane to gain access to the vertebra.

While probably not necessary, once the percutaneous incisions 62a-f are formed, blunt finger dissection can optionally be used, as shown in FIGS. 5A-5B, to separate the longissimus thoracis LT and multifidus muscles M, thereby exposing the facet and the junction of the transverse process and superior articular process.

Figure 5C:
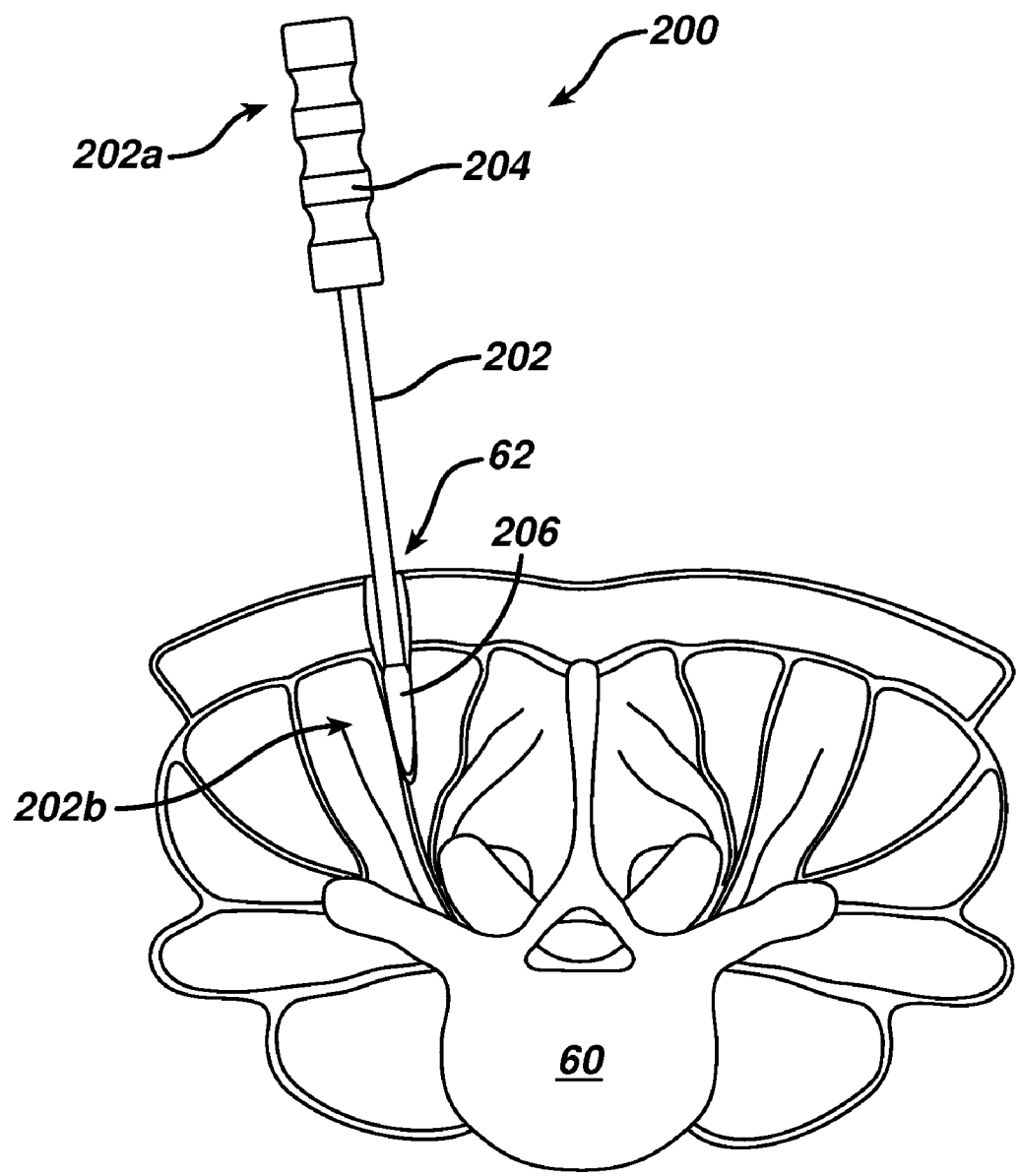
FIG. 5C is an end view of the vertebra shown in FIG. 5A showing another embodiment of a technique using a tool for separating the muscles along the dissected muscle plane to gain access to the vertebra.
Figure 5E:
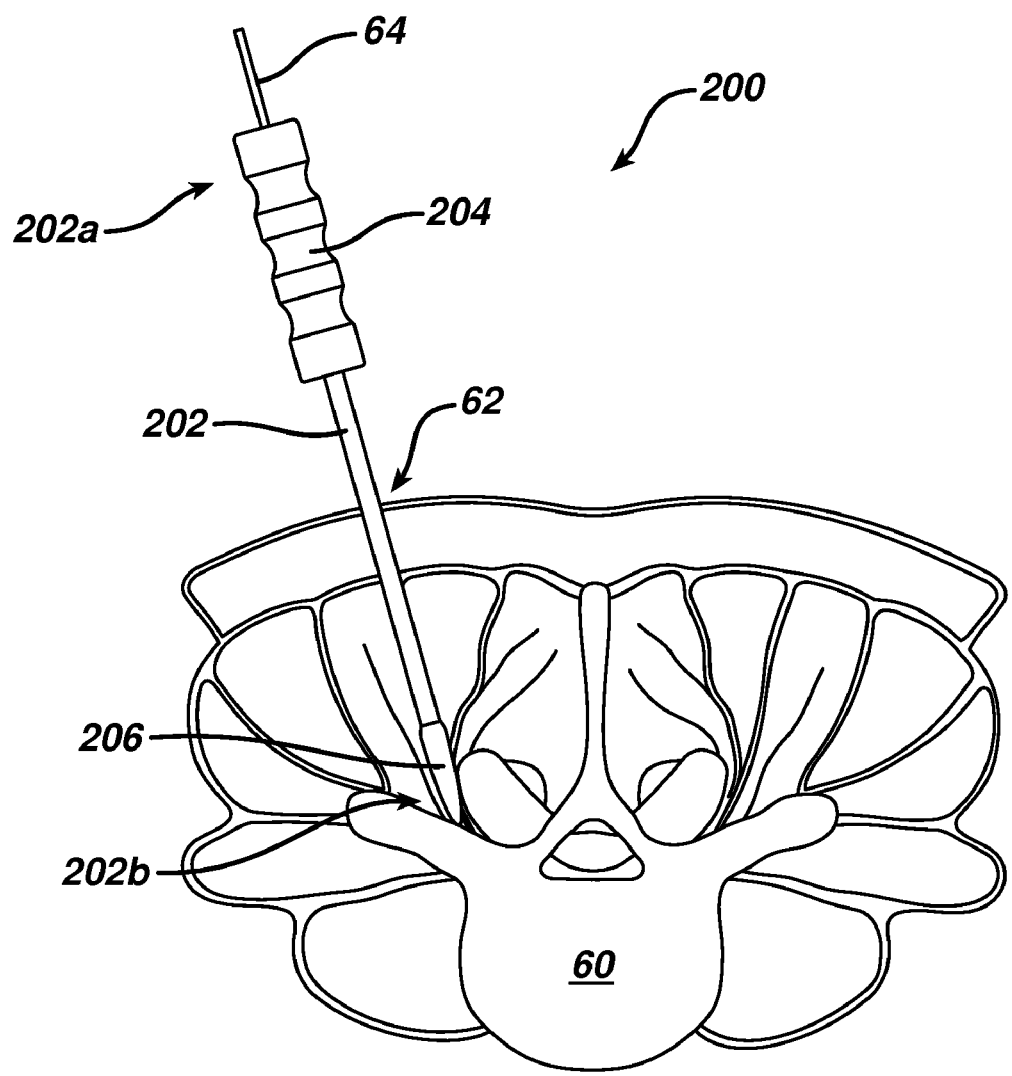
FIG. 5E is an end view of the vertebra shown in FIG. 5C showing placement of a guide wire through the tool and into the patient's vertebra.

FIGS. 5C-5E illustrate another exemplary technique for separating the longissimus thoracis and multifidus muscles using a blunt tool 200, which is shown in more detail in FIGS. 5F-5G. Referring first to FIGS. 5F-5G, the tool 200 generally includes a rigid elongate shaft 202 having proximal and distal ends 202a, 202b. The shaft 202 also includes a lumen 202c extending therethrough between the proximal and distal ends 202a, 202b for receiving a guide wire, such as a k-wire. The lumen 202c may be sized to receive a guidewire 202c delivered through the lumen 202c. The proximal end 202a may include a handle 204 formed therein to facilitate grasping of the tool 200. The handle 204 can have virtually any shape and size. For example, as shown in FIGS. 5F-5G, the handle 204 in the exemplary embodiment has a generally elongate cylindrical shape and it includes ridges 204a formed thereon to facilitate gripping of the device.

The distal end 202b of the tool 200 includes a blunt member 206 formed thereon. The blunt member 206 may be adapted, e.g., sized and shaped, to separate muscles along a muscle plane while concomitantly minimizing trauma to the separated muscles. While the shape of the blunt member 206 can vary, in an exemplary embodiment, as shown, the blunt member 206 has a substantially elongate rectangular shape with opposed front and back surfaces 206a, 206b. The width between the front and back surfaces 206a, 206b may taper or decreases in a distal direction such that the distal-most width $w_{b2}$ is less than the proximal-most width $w_{b1}$. Such an exemplary configuration facilitates insertion of the blunt member 206 between tissue, e.g., muscle, to allow the tissue to be separated. The width $w_s$ extending between opposed side edges of the front and back surfaces 206a, 206b can also vary, but in an exemplary embodiment, as shown, the width $w_s$ remains constant along the length of the front and back surfaces 206a, 206b.

While not shown, the tool 200 can also optionally include an inner tube disposed within the elongate shaft 202 for preparing the vertebra. In particular, the inner tube can be slidably disposed within the elongate shaft 202 to allow the inner tube to be moved distally into bone to create a divot in the vertebra, thereby preparing the bone for an awl or tap. The tool 200 can also optionally serve as a drill guide. In particular, the elongate shaft 202 can have an inner diameter that is adapted to receive a drill therethrough to guide the drill toward and into the vertebra. The shaft 202 also serves as a protective cannula for the drill, inhibiting contact between the drill and the muscles surrounding the tool 200. A person having ordinary skill in the art will appreciate that the tool 200 can have a variety of other configurations, and that the tool 200 can be adapted for a variety of other uses.

Referring now to FIGS. 5C-5E, the exemplary tool 200 is shown in use. As shown, after the percutaneous incisions 62a-f are formed, as previously described, the blunt member 206 of the dissection tool 200 may be inserted through an incision 62. The incision 62 may be deep enough to allow the fat layer between the longissimus thoracis and multifidus muscles to be located. Once located, the tool 200 may be manipulated to separate or split the longissimus thoracis and multifidus muscles, thereby exposing the facet and the junction of the transverse process and superior articular process. Once the tool 200 is positioned adjacent to or against the vertebra 60, as shown in FIG. 5D, a guide wire, e.g., a k-wire 64, can be inserted through the lumen 202c in the tool 200 to position a distal end of the k-wire 64 at or within the vertebra 60, as shown in FIG. 5E. Fluoroscopy or other imaging may be used to facilitate proper placement of the k-wire 64. The tool 200 can then be removed from the k-wire 64, leaving the k-wire 64 to serve as a guide for various other devices, which will be described in more detail below. This procedure can be repeated at each incision 62a-f to facilitate placement of multiple spinal anchors.

Where tool 200 is not used, a guide wire, e.g., k-wire 64, can be implanted, either prior to or after formation of the incision, at each spinal anchor implant site. As shown in FIG. 6, the k-wire 64 preferably extends between the muscles and into the vertebra at the desired entry point of the spinal anchor. Fluoroscopy can be used to facilitate proper placement of the k-wire 64.

Figure 7:
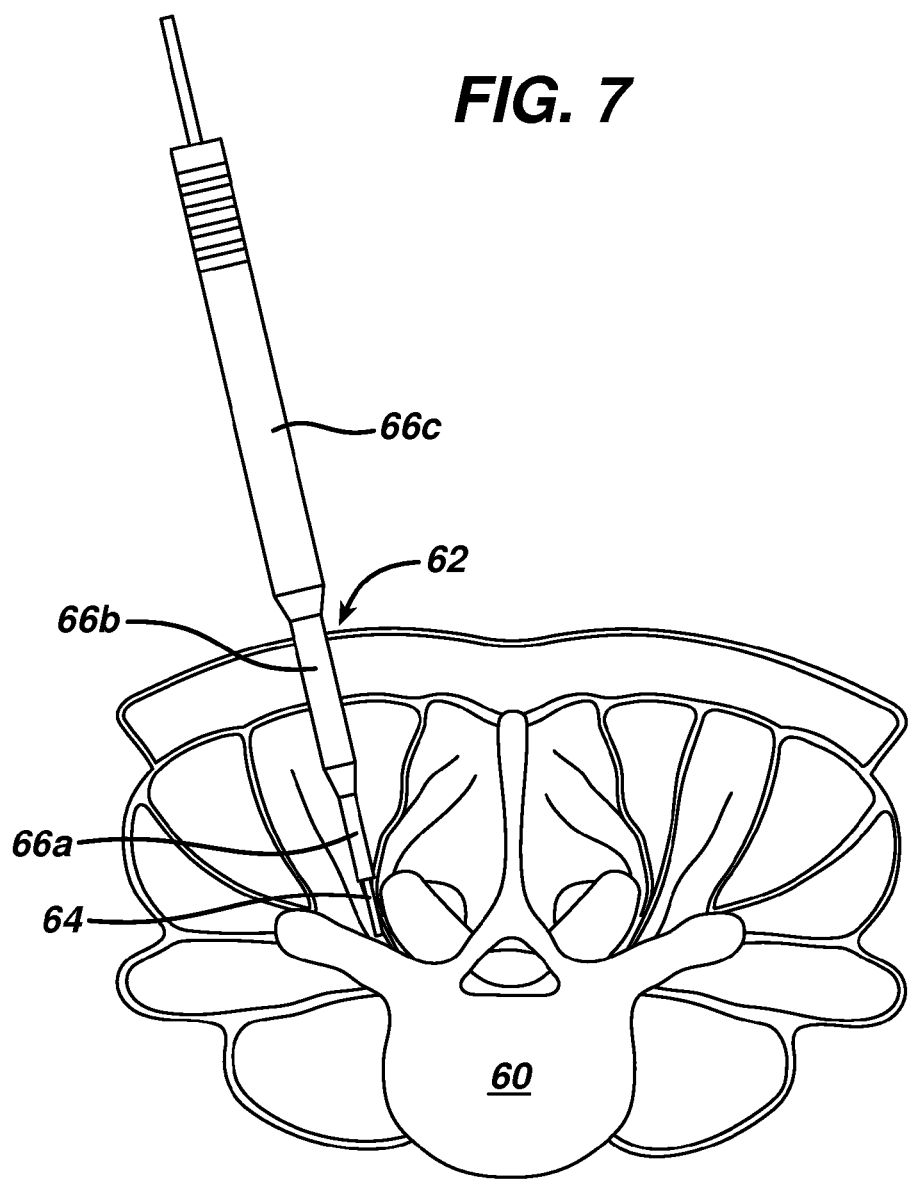
FIG. 7 is an end view of the vertebra shown in FIG. 6 having an obturator and several dilators disposed over the guide wire to dilate the tissue and muscles.

The opposed ends of the incision can then be dilated to provide a pathway for delivery of a spinal anchor to each implant site. FIG. 7 illustrates dilation at one end of the incision 62 using an obturator 66a having several dilators 66b, 66c of increasing size placed there over. The dilators 66b, 66c are delivered over the obturator 66a and k-wire 64 to essentially stretch the skin around the incision 62 and to expand the pathway to the anchor site.

Figure 8:
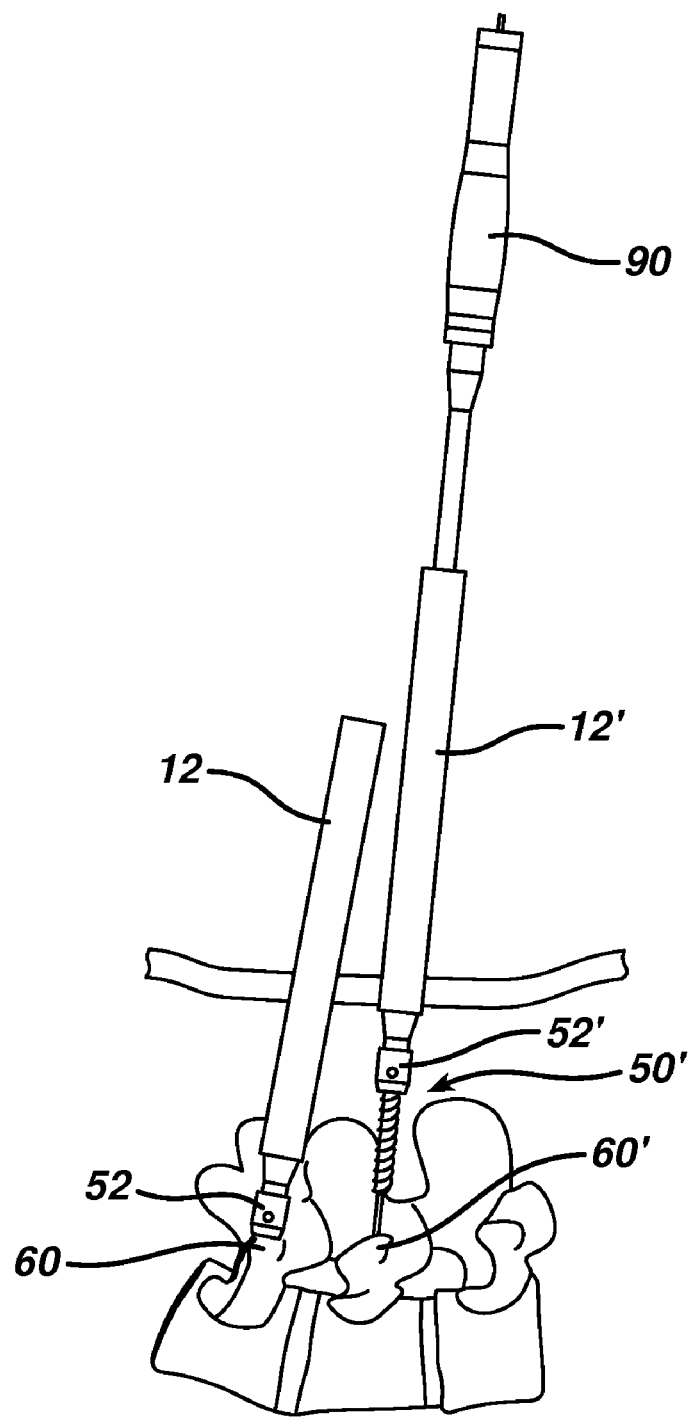
FIG. 8 is perspective view of a first spinal anchor implanted in a vertebra and having a percutaneous access device coupled thereto and extending through a percutaneous incision formed in the patient's tissue surface, and a second spinal anchor being implanted into an adjacent vertebra and having a percutaneous access device coupled thereto with a driver tool extending therethrough.

Once the incision 62 is dilated to the proper size, an anchor can be delivered to each anchor site, as shown in FIG. 8. This procedure typically involves preparation of the vertebra 60 using one or more bone preparation instruments, such as drills, taps, awls, burrs, probes, etc. While not always necessary, one or more cannulae can be used to provide a pathway from the incision 62 to the anchor site for insertion of the bone preparation instruments and/or the anchor. In an exemplary embodiment, a relatively small cannula is used to introduce bone preparation instruments into the surgical site. The incision 62 can then be further dilated, and the small cannula can be replaced with a larger cannula that is adapted to receive or mate to the anchor.

Once the vertebra 60 is prepared, a spinal anchor can be implanted at each implant site. An access device 12, 12' can be mated to each anchor 50, 50' after insertion of the anchor 50, 50' into bone 60, 60', but more preferably each percutaneous access device 12, 12' is attached to the anchor 50, 50' prior to insertion of the anchor 50, 50' into bone 60, 60' to provide a passageway for a driver tool for driving the anchor 50 into bone 60, 60'. FIG. 8 illustrates anchor 50 implanted in a first vertebra 60 and having access device 12 attached thereto. While not shown, the anchor 50 is preferably cannulated to allow the k-wire 64 to extend through the anchor 50 and the access device 12 to guide the devices 50, 12 toward the implant site. FIG. 8 further illustrates a second anchor 50' having an access device 12' mated thereto. As shown, the screw 50' is about to be implanted in a second vertebra 60' that is adjacent to the first vertebra 60. Once the screw 50' is positioned adjacent to the vertebra 60', a driver tool 90 can be positioned through the access device 12' and coupled to the receiver head 52' of the screw 50' to drive the screw 50' into the vertebra 60'.

In another embodiment, a sleeve can be placed over each access device 12, 12', either prior to or after the devices 12, 12', 50, 50' are implanted, to prevent the devices 12, 12' from becoming disengaged from the anchors 50, 50' to which they are attached. The sleeve 100, which is partially illustrated in FIG. 3B, is preferably in the form of a cannula that has substantially the same configuration as each access device 12, 12'. The use of a sleeve is particularly desirable where the access devices 12, 12' utilize pin members that engage corresponding detents formed on an outer surface of each screw head 52, 52', as the sleeve will prevent the pin members from becoming disengaged from the detents. The sleeve can also optionally serve as an access device, allowing access devices 12, 12' to be detached and removed from the anchors 50, 50'.

Figure 9:
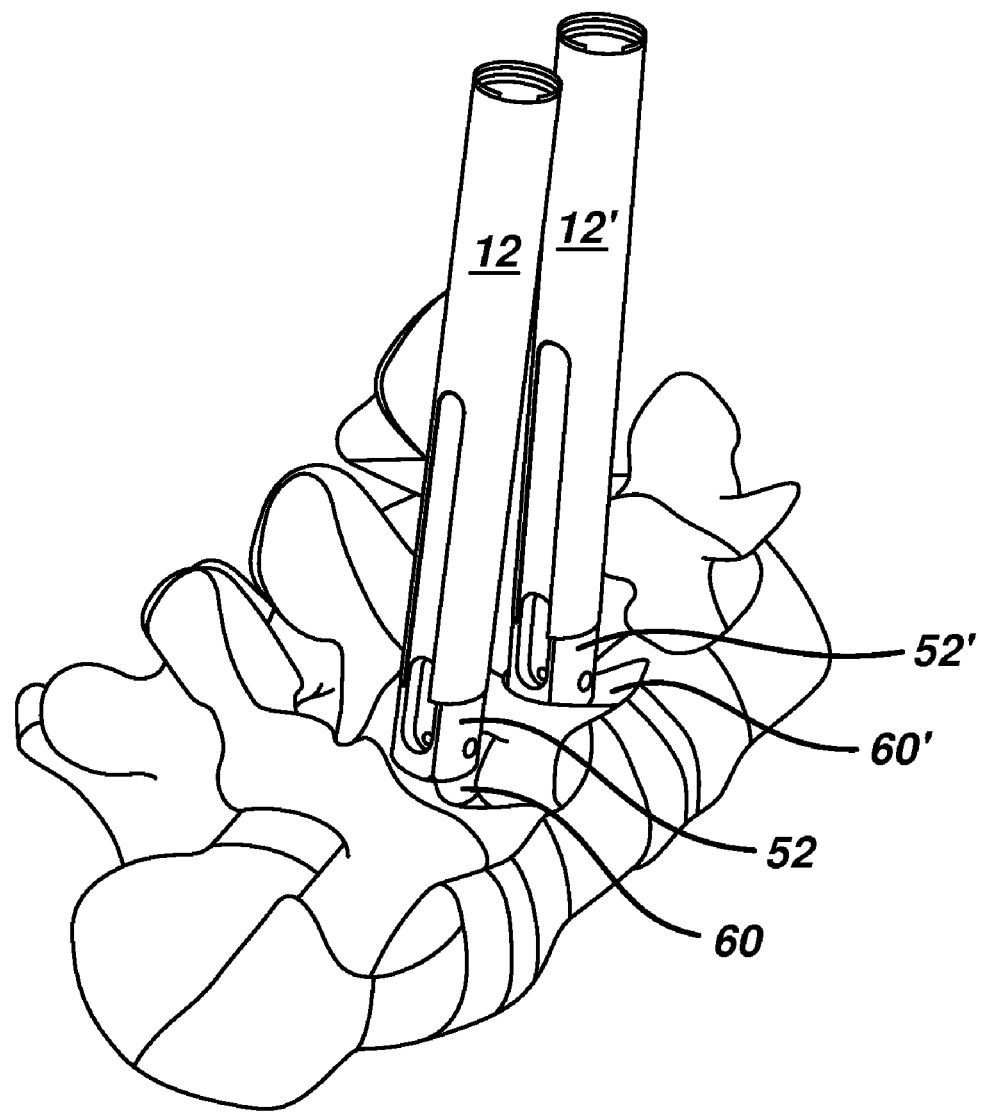
FIG. 9 is a perspective view of two percutaneous access devices attached to spinal anchors that are disposed within adjacent vertebrae in a patient's spinal column.

After the anchors 50, 50' are implanted, a spinal fixation element 70 is delivered to the anchor site. This can be achieved by introducing the spinal fixation element 70 through one of the percutaneous access devices 12, 12' that is attached to the anchor 50, 50', or through some other percutaneous access device that provides a pathway to the anchor(s) 50, 50'. As shown in FIG. 9, a spinal fixation element, e.g., a spinal rod 70, is introduced into device 12 in a first, lengthwise orientation, such that the spinal fixation element 70 is substantially parallel to the longitudinal axis L of the access device 12. Where the fixation element has a curved orientation or it has some other configuration, it is understood that the fixation element is in the "substantially parallel" orientation when it is positioned lengthwise through the percutaneous access device.

Figure 10:
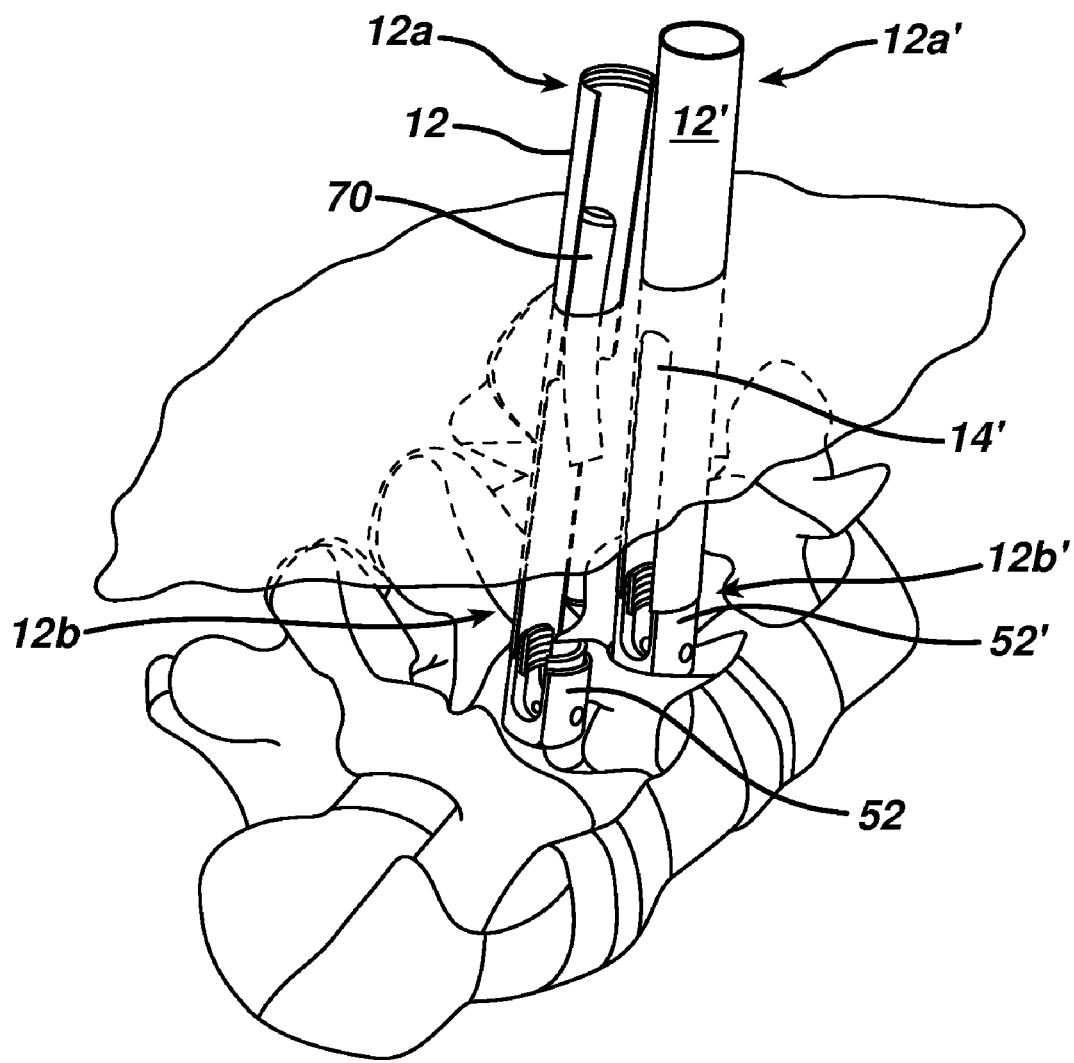
FIG. 10 illustrates a method for introducing a spinal fixation element through a partially cut-away view of one of the percutaneous access devices shown in FIG. 9.
Figure 11:
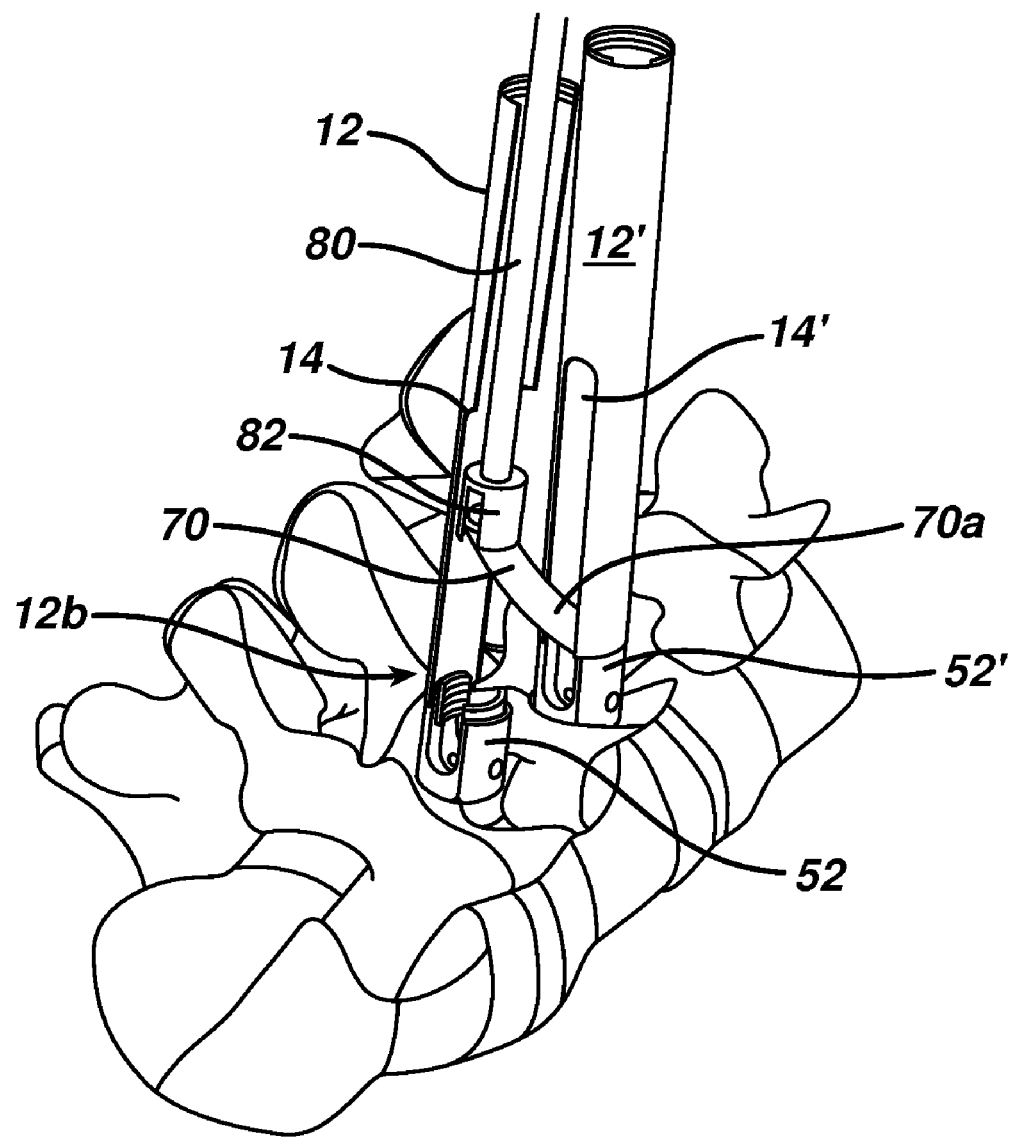
FIG. 11 is a perspective view of the spinal fixation element shown in FIG. 10 being advanced in toward the spinal anchors using a pusher device.

The spinal fixation element 70 is then moved distally toward the distal end 12b of the percutaneous access device 12, as shown in FIGS. 10 and 11. Movement of the spinal fixation element 70 can be achieved using a manipulator device 80. The manipulator device 80 can have a variety of configurations, but it should be effective to allow controlled movement of the fixation element 70. A person skilled in the art will appreciate that a variety of other techniques can be used to guide the spinal fixation element 70 through the percutaneous access device 12 and to position the spinal fixation element 70 in relation to one or more anchors 50, 50'. Moreover, the spinal fixation element 70 can have a variety of configurations to facilitate insertion through a percutaneous access device. By way of non-limiting example, U.S. Publication No. 2005/0131407 entitled "Flexible Spinal Fixation Elements," and filed on Dec. 16, 2003, discloses a spinal fixation element that can be flexed as it is passed through a percutaneous access device, thereby allowing the spinal fixation element to transition from the first orientation to the second orientation. The application also discloses techniques for delivering the spinal fixation element along a guide wire or cable, thus eliminating the need for a manipulator device. Other spinal fixation elements suitable for use with the present invention, in addition to mechanical and flexible fixation elements, include, for example, inflatable fixation elements such as those disclosed in U.S. Patent Publication No. 2002/0068975, now U.S. Pat. No. 6,749,614, entitled "Formable Orthopedic Fixation System with Cross Linking" by Teitelbaum et al., U.S. Patent Publication No. 2002/0082600, now U.S. Pat. No. 6,899,713, entitled "Formable Orthopedic Fixation System" by Shaolian et al., and U.S. Patent Publication No. 2002/0198526, now U.S. Pat. No. 6,964,667, entitled "Formed In Place Fixation System With Thermal Acceleration" by Shaolian et al., each of which are hereby incorporated by reference in their entirety.

Figure 12:
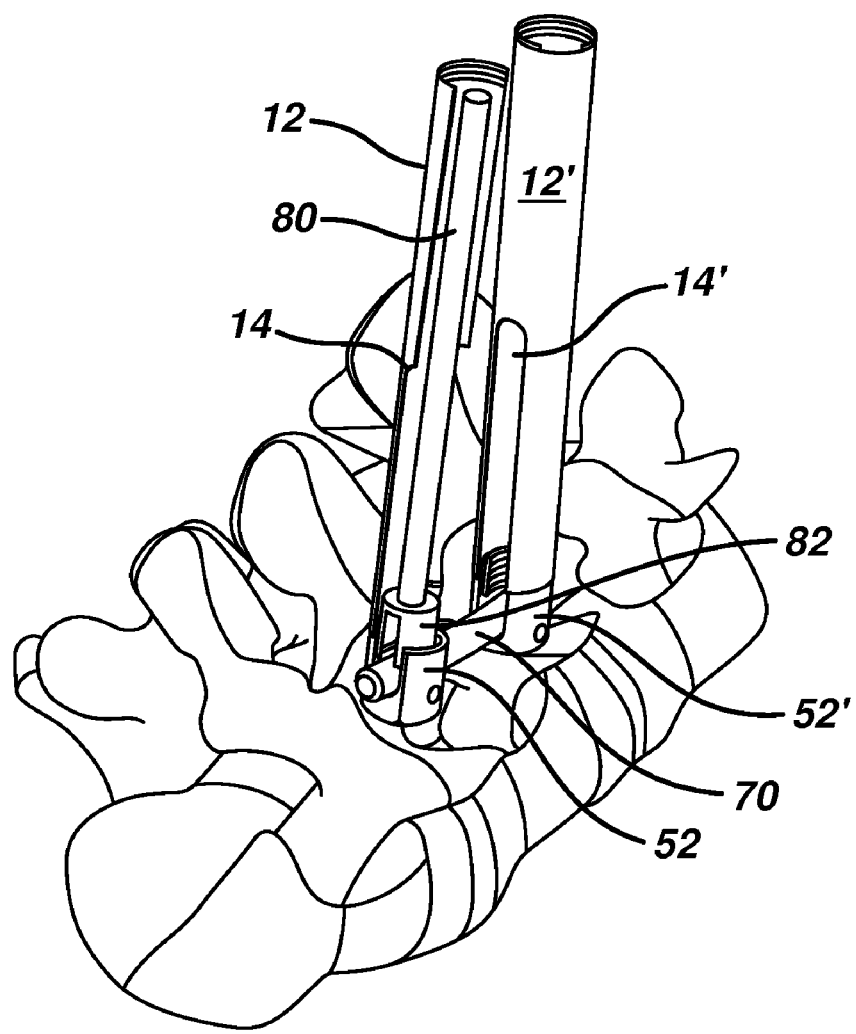
FIG. 12 is a perspective view of the spinal fixation element shown in FIG. 11 after it is fully positioned within receiver heads of the adjacent spinal anchors.

Referring now to FIGS. 11 and 12, as the spinal fixation element 70 approaches the distal end 12b of the access device 12, the spinal fixation element 70 can be manipulated to cause the spinal fixation element 70 to assume a second orientation that is different from the first orientation, and more preferably that is substantially parallel to the patient's spinal column and/or transverse to the first orientation. It is understood that the angle of the fixation element 70 in the second orientation will vary depending on the type of fixation device being implanted, as well as the orientation of the access device 12, which can vary throughout the surgical procedure since the access device 12 can be positioned at several angles with respect to the patient's spinal column.

During transition of the spinal fixation element 70 from the first orientation to the second orientation, a leading end of the spinal fixation element 70 should be subcutaneously positioned. Where the access device 12 includes slots or openings (only one opening 14 is shown), the opening(s) 14 can be used to facilitate movement of the spinal fixation element 70 into the second orientation as they will allow the spinal fixation element 70 to extend therethrough during rotation. This may not be necessary, however, depending on the length of the openings 14, the length of the spinal fixation element 70, and/or the configuration of the spinal fixation element 70. As shown in FIGS. 11 and 12, only the leading end 70a of the spinal fixation element 70 exits the percutaneous access device 12 through one of the openings 14.

Referring to FIG. 12, manipulation of the spinal fixation element 70 is continued until the spinal fixation element 70 is positioned in relation to one or more spinal anchors. Depending on the type of spinal anchor used, the fixation element can be positioned to be directly or indirectly mated to the spinal anchor. As shown in FIG. 12, the fixation element 70 is fully seated in the receiver heads 52, 52' of the adjacent spinal anchors 50, 50'. The manipulator device 80, if used, can then be removed from the access device 12.

In another embodiment, the percutaneous access device 112 shown in FIGS. 3A and 3B can be used to facilitate introduction of a spinal fixation element into a surgical anchor site. As previously stated, access device 112 includes a guide member 20 formed therein to direct the spinal fixation element 70 from the first orientation to the second orientation. This is illustrated in FIGS. 13-16. As shown, as the spinal fixation element 70 is moved distally to come into contact with the guide member 120, the guide member 120 causes the spinal fixation element 70 to rotate and extend toward the opening 114 in the percutaneous access device 112. As a result, the spinal fixation element 70 is directed into the second orientation, whereby it can be positioned in or adjacent to the receiver heads 52, 52' of the adjacent spinal implants 50, 50'.

Referring back to FIG. 12, once the spinal fixation element 70 is fully seated in the receiver heads 52, 52' of the adjacent spinal anchors 50, 50', the pusher shaft 80, if used, can then be removed or detached from the spinal fixation element 70, and a closure mechanism can be applied to one or both receiver heads 52, 52' to retain the spinal fixation element 70 therein. In an exemplary embodiment, however, a compression tool 100 is used to compress the access devices 12, 12' toward one another prior to applying a closure mechanism to each anchor 50, 50'. The closure mechanism(s) can, however, be partially applied before compression.

Figure 17:
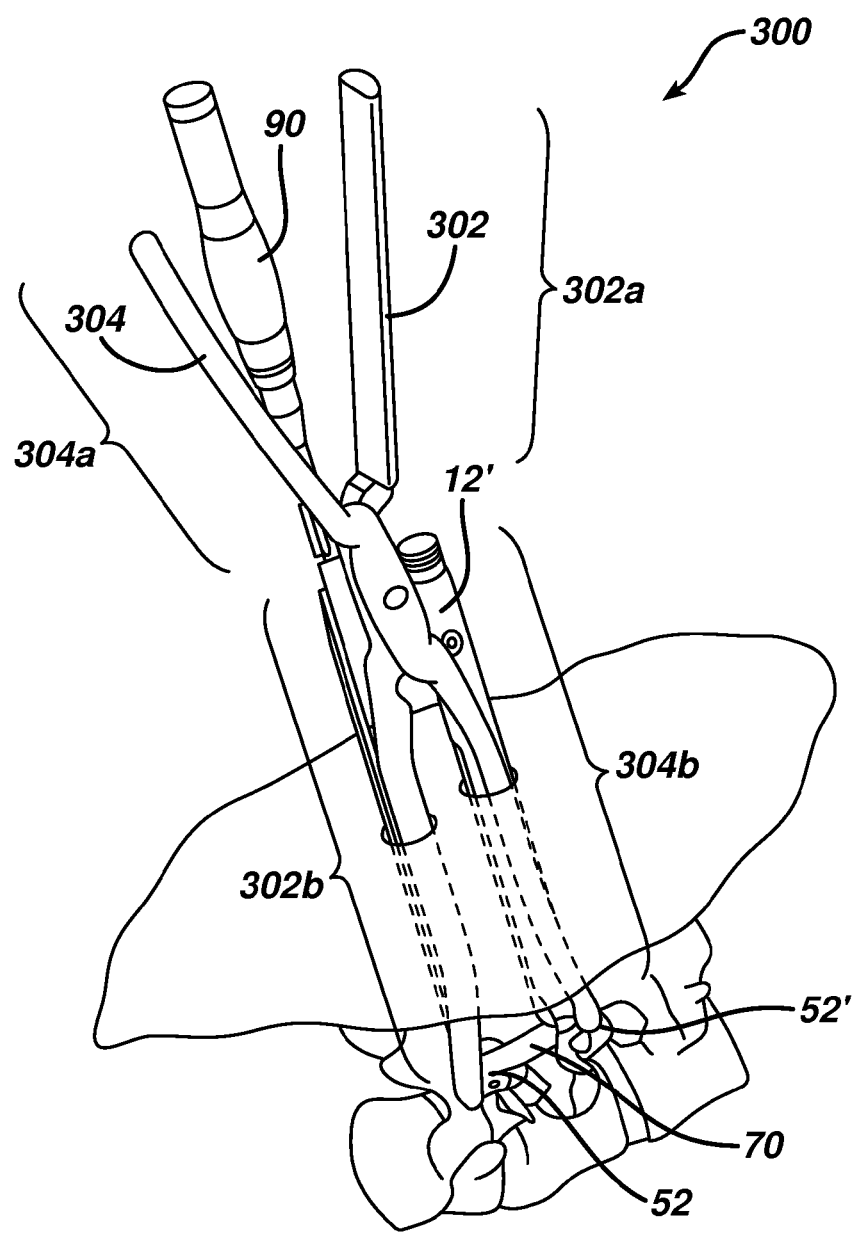
FIG. 17 is a perspective view of a compression tool positioned around the percutaneous access devices shown in FIG. 12 and compressing the devices toward one another, and a closure mechanism being applied through one of the percutaneous access devices to lock the spinal fixation element in relation to the spinal anchor.

An exemplary compression tool 300 is shown in FIG. 17, and in general it includes opposed arms 302, 304 that are pivotally coupled to one another at a substantial mid-point thereof such that each arm 302, 304 includes a distal portion 302b, 304b that is adapted to be disposed around a percutaneous access device 12, 12', and a proximal, handle portion 302a, 304a. The device 300 can also include a fulcrum (not shown) that is disposed between the arms 302, 304 to facilitate controlled movement of the arms 302, 304 with respect to one another. In use, the distal portion 302b, 304b of each arm 302, 304 is placed around an access device 12, 12', preferably around the distal end 12b, 12b' of each device 12, 12' and/or around the head 52, 52' of each anchor 50, 50'. The proximal, handle portions 302a, 304a are then brought toward one another to move the access devices 12, 12' toward one another, preferably while maintaining relative spacing therebetween, as shown in FIG. 17.

Figure 13:
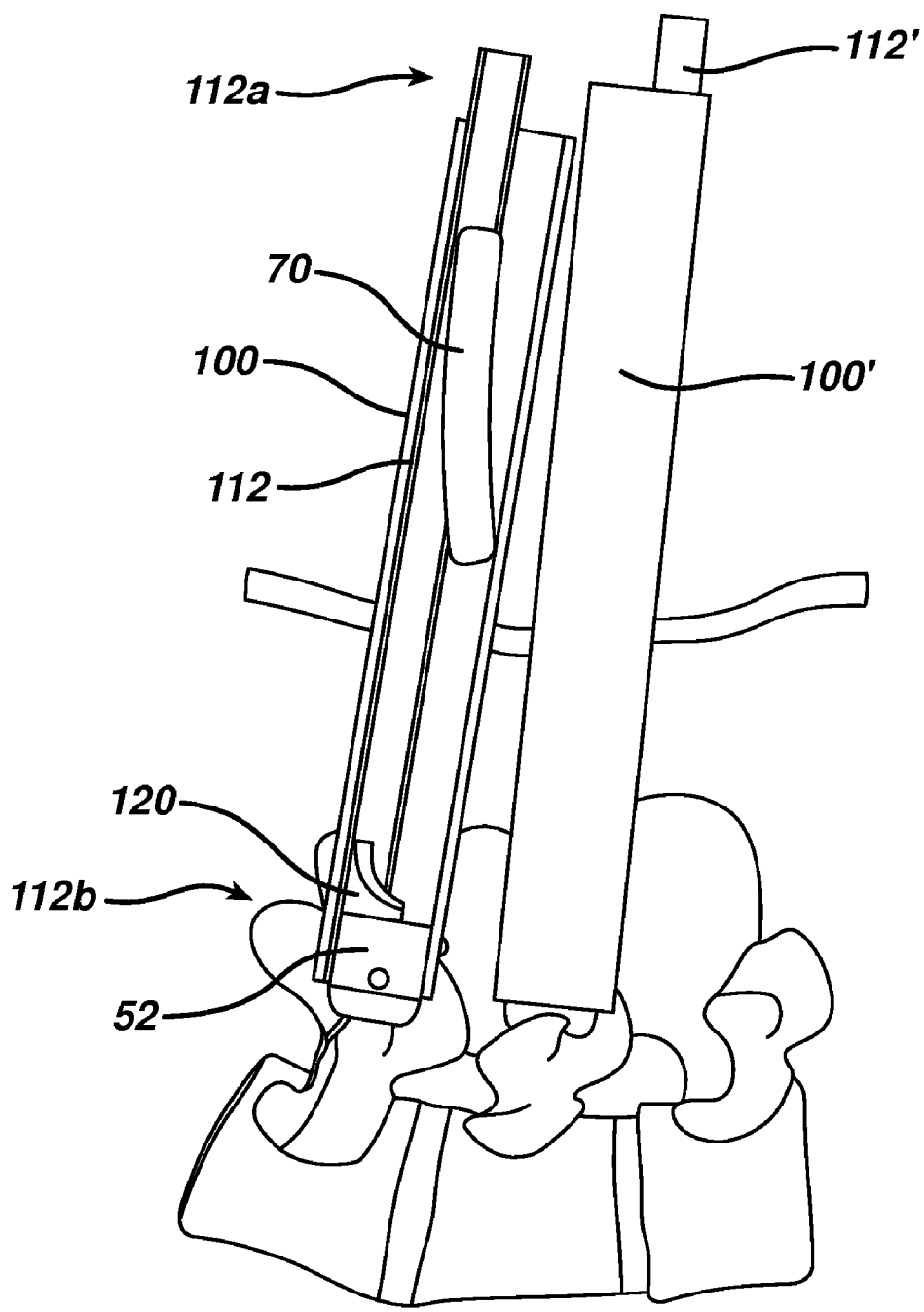
FIG. 13 illustrates a method for introducing a spinal fixation element through a partially cut-away view of the percutaneous access device shown in FIGS. 3A and 3B.
Figure 14:
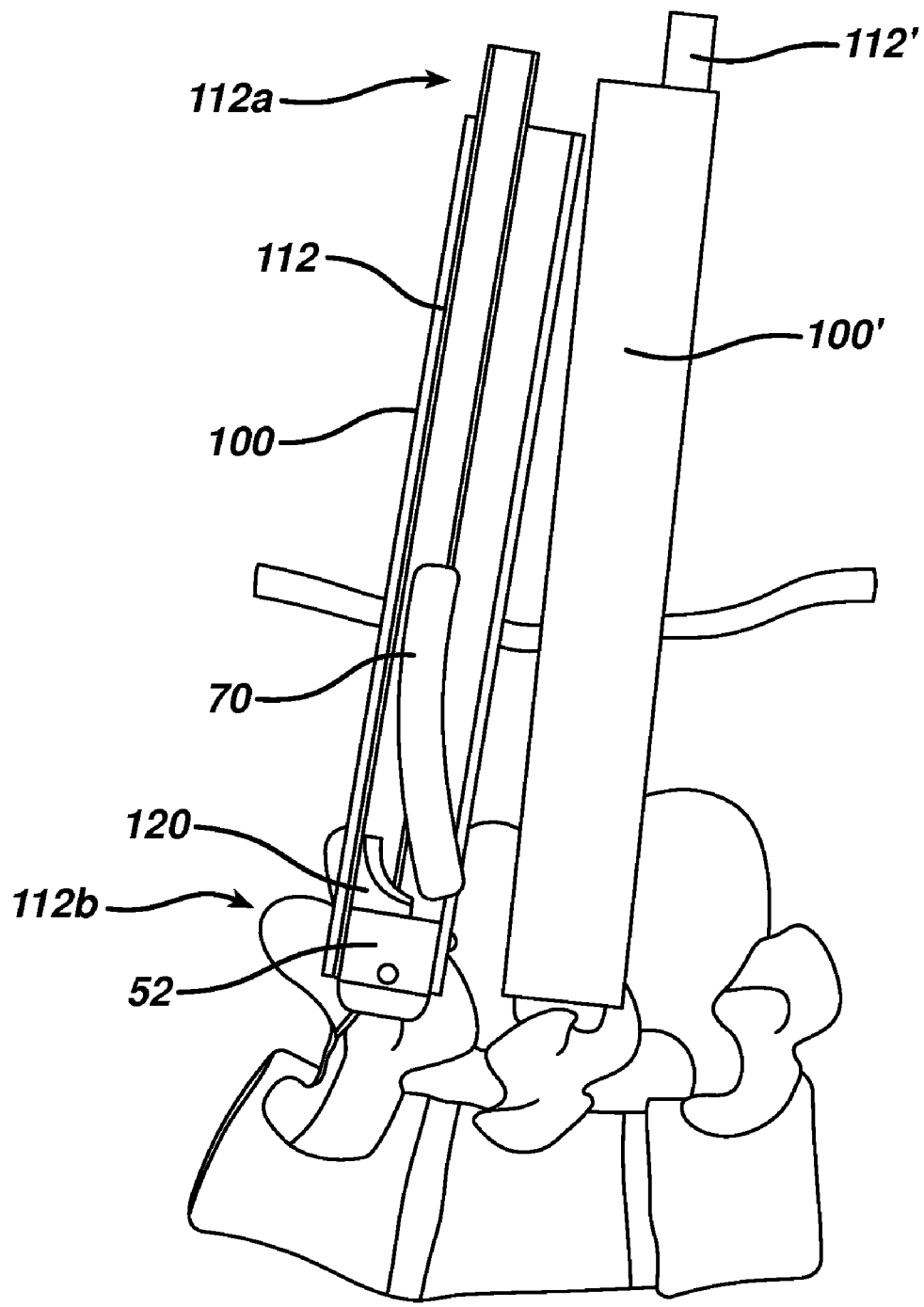
FIG. 14 is a perspective view of the spinal fixation element shown in FIG. 13 being advanced toward the spinal anchors using a pusher device.
Figure 15:
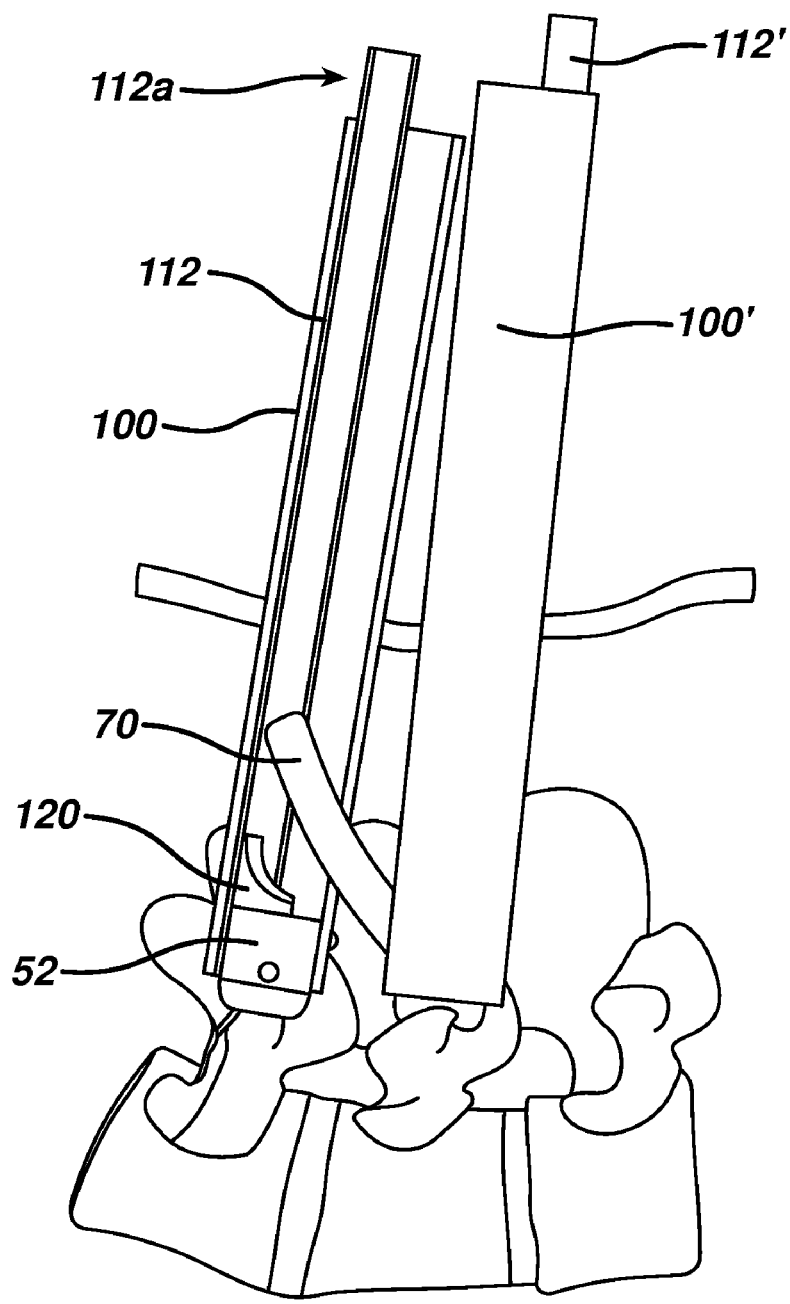
FIG. 15 is a perspective view of the spinal fixation element shown in FIG. 14 advanced further toward the receiver heads of the adjacent spinal anchors.
Figure 16:
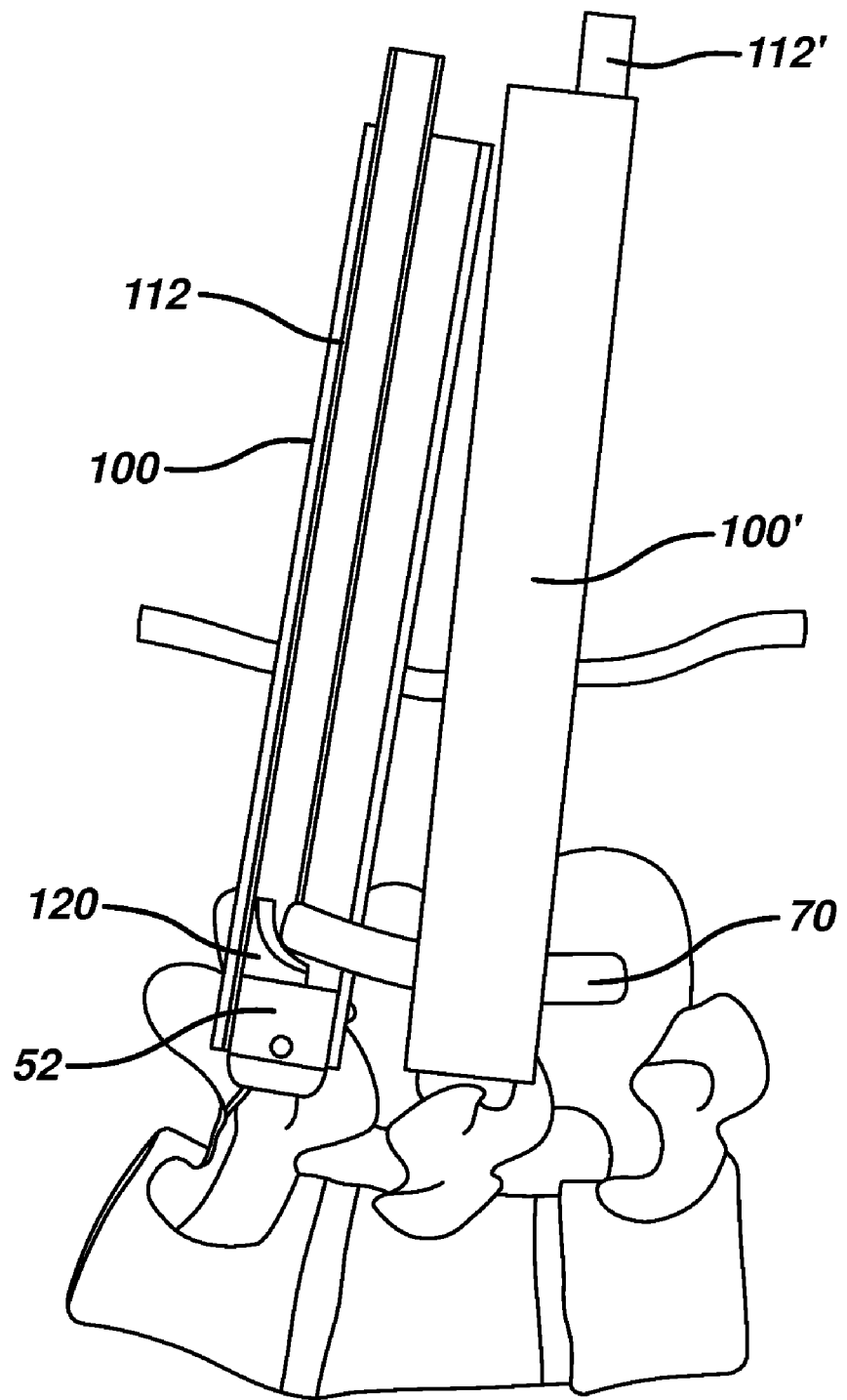
FIG. 16 is a perspective view of the spinal fixation element shown in FIG. 15 about to be disposed within the receiver heads of the adjacent spinal anchors.

Once properly positioned, a closure mechanism can be applied, preferably via the access devices 12, 12', to each anchor head 50, 50' to retain the spinal fixation element 70 within the receiver heads 52, 52'. A variety of closure mechanisms and tools for delivering closure mechanisms are known in the art and they can be used with the present invention. By way of non-limiting example, FIG. 13 illustrates driver tool 90 disposed through access device 12 for applying a closure mechanism, such as a set screw, to the receiver head 52 of the spinal anchor 50 to lock the spinal fixation element 70 with respect to the spinal anchor 50. This step can be repeated for the adjacent spinal anchor(s).

A person skilled in the art will appreciate that the spinal fixation element 70 does not need to be directly attached to each anchor 50, 50', and that it can be indirectly attached to the anchors 50, 50' using, for example, a band clamp, or slotted or offset connectors.

Once the fixation element 70 is secured in relation to the implants 50, 50', the access devices 12, 12' can be removed from the implants 50, 50', leaving only minimally invasive percutaneous incisions in the patient where each access device 12, 12' was introduced. This is particularly advantageous in that it reduces the amount of trauma caused to the patient, and it minimizes the damage to muscle surrounding the surgical site.

As previously stated, a person skilled in the art will appreciate that the method can be performed in any sequence using any of the steps. Moreover, the access devices of the present invention can be used to deliver multiple spinal fixation elements simultaneously or sequentially, and/or to perform a variety of other surgical procedures not illustrated or described herein.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A minimally invasive surgical method, comprising:
   forming an incision through tissue located adjacent to a vertebra in a patient's spinal column;
   inserting a cannulated tool having an elongate shaft with a blunt-tip through the incision while manipulating the blunt tip along a muscle plane extending between the incision and the vertebra to separate the muscles without cutting the muscles, the blunt tip having opposed substantially planar surfaces;
   advancing a guidewire through a lumen in the tool with the tool extending from the skin incision to the vertebra to thereby position a distal end of the guidewire in contact with the vertebra;
   removing the tool leaving the guidewire extending from the incision to the vertebra; and
   advancing a spinal anchor having a percutaneous access device mated thereto over the guidewire to deliver the spinal anchor to the vertebra.

2. The method of claim 1, further comprising advancing a spinal screw over the guidewire and implanting the spinal screw in the vertebra.

3. The method of claim 1, further comprising, after removing, advancing a plurality of dilators over the guidewire.

4. A minimally invasive surgical method, comprising:
   forming an incision through tissue located adjacent to a vertebra in a patient's spinal column;
   inserting a cannulated tool having an elongate shaft with a blunt tip through the incision while manipulating the blunt tip along a muscle plane extending between the incision and the vertebra to separate the muscles without cutting the muscles, the blunt tip having opposed substantially planar surfaces;
   advancing a guidewire through a lumen in the cannulated tool with the cannulated tool extending from the skin incision to the vertebra to thereby position a distal end of the guidewire in contact with the vertebra;
   removing the tool leaving the guidewire extending from the incision to the vertebra;
   advancing a cannula over the guidewire;
   removing the guidewire from the cannula such that the cannula defines a working pathway extending therethrough from the skin incision to the vertebra; and
   delivering a spinal implant through the cannula.

5. The method of claim 4, wherein the spinal implant comprises a spinal fixation rod.

6. The method of claim 5, wherein the spinal fixation rod is delivered through the cannula in an orientation substantially parallel to a longitudinal axis of the cannula.

7. The method of claim 4, wherein the cannula is mated to a spinal anchor and the spinal anchor is advanced over the guidewire with the cannula.

8. A minimally invasive surgical method, comprising:
   forming an incision in tissue;
   inserting a blunt tip of a cannulated tool through the incision and manipulating the tool to separate a naturally-occurring muscle plane between longissimus thoracis and multifidus muscles, thereby forming a pathway between the muscles to a vertebra, the blunt tip having opposed substantially, planar surfaces;
   inserting a guidewire through a lumen in the cannulated tool to position a distal end of the guidewire at the vertebra;
   removing the tool leaving the guidewire extending through the pathway; and
   advancing a spinal implant over the guidewire to deliver the spinal implant to the vertebra.

9. The method of claim 8, further comprising inserting a plurality of dilators over the guidewire to dilate tissue surrounding the guidewire.

10. The method of claim 9, further comprising inserting a cannula over the plurality of dilators and removing the dilators.

11. The method of claim 10, further comprising placing a fixation element through the cannula in an orientation substantially parallel to a longitudinal axis of the cannula.

* * * * *